US008785148B2

(12) United States Patent
Sauer-Budge et al.

(10) Patent No.: US 8,785,148 B2
(45) Date of Patent: Jul. 22, 2014

(54) METHOD AND DEVICE FOR RAPID DETECTION OF BACTERIAL ANTIBIOTIC RESISTANCE/SUSCEPTIBILITY

(75) Inventors: Alexis Sauer-Budge, Lincoln, MA (US); Andre Sharon, Newton, MA (US); Maxim Kalashnikov, Brighton, MA (US); Holger Wirz, Medford, MA (US)

(73) Assignees: Fraunhofer, USA, Inc., Plymouth, MI (US); Trustees of Boston University, Boston, MA (US)

( * ) Notice: Subject to any disclaimer, the term of this patent is extended or adjusted under 35 U.S.C. 154(b) by 0 days.

(21) Appl. No.: 13/283,892

(22) Filed: Oct. 28, 2011

(65) Prior Publication Data

US 2012/0122831 A1   May 17, 2012

Related U.S. Application Data

(63) Continuation of application No. PCT/US2010/033523, filed on May 5, 2010.

(60) Provisional application No. 61/175,605, filed on May 5, 2009.

(51) Int. Cl.
*C12Q 1/18* (2006.01)
*G01N 33/554* (2006.01)
*G01N 33/569* (2006.01)
*G01N 33/53* (2006.01)

(52) U.S. Cl.
USPC .......... 435/32; 435/7.32; 435/7.33; 435/7.34; 435/7.37; 435/7.71; 435/7.72

(58) Field of Classification Search
USPC .......... 435/6.15, 7.32, 7.33, 7.34, 7.37, 7.71, 435/7.72, 32
See application file for complete search history.

(56) References Cited

U.S. PATENT DOCUMENTS

| 7,341,841 | B2 | 3/2008 | Metzger et al. | |
| 7,648,830 | B2 * | 1/2010 | Squirrell et al. | 435/32 |
| 2002/0025537 | A1 * | 2/2002 | Bylina et al. | 435/7.1 |
| 2004/0248199 | A1 * | 12/2004 | Squirrell et al. | 435/7.1 |

FOREIGN PATENT DOCUMENTS

| EP | 0322591 | 1/1988 |
| WO | 92/16648 | 10/1992 |
| WO | 03/078654 | 9/2003 |
| WO | 2008107881 | 9/2008 |
| WO | 2010127278 | 11/2010 |

OTHER PUBLICATIONS

Lebaron, P., et al. Applied and Environmental Microbiology. vol. 64, pp. 2697-2700. Published 1998.*
Farr, S.B., et al. Microbiological Reviews. vol. 55, pp. 561-585. Published 1991.*
Matlin, A. Ann. NY Acad. Sci. vol. 665 pp. 1-15. Published 1992.*
Molecular Probes SYTOX Green Nucleic Acid Stain Product Page. Published 2006.*
Boles, B.R., et al. PNAS vol. 105, pp. 12503-12508. Publishd 2008.*
Moskowitz, S.M. et al., Journal of Clinical Microbiology vol. 42, pp. 1915-1922. Published 2004.*
SYTOX product page, Published 2006.*
Matin, A. et al. (Ann. NY Acad. Sci. vol. 665, pp. 1-15. Published 1992.*
Shenkman, et al., Infect Immun (2001) 69(7): pp. 4473-4478.
Steen, et al., Cytometry (1982) 2(4): pp. 249-257.
Suller, et al., J Antimicrob Chemother (1997) 40(1): pp. 77-83.
Thomas, et al., Cell (2002) 109(7): pp. 913-923.
Utsui, Y. et al., Antimicrob Agents Chemother (1985) 28(3): pp. 397-403.
Vincent, et al., Presse Med (1985) 14(32): pp. 1697-1700, abstract only.
Waxman, et al., Annu Rev Biochem, (1983), 52: pp. 825-869.
Wu, et al., Appl Microbiol Biotechnol (2002) 58(2): pp. 175-177.
Wu, et al., Antimicrob Agents Chemother (2003) 47(11): pp. 3407-3414.
Mohamed, et al., Infect Immun (1999) 67(2): pp. 589-594.
Baggett, H. C., et al. J Infect Dis, (2004) 189(9): pp. 1565-1573.
Barenfanger, J., et al., J Clin Microbiol (1999) 37(5): pp. 1415-1418.
Becker, K., et al., J Clin Microbiol (2006) 44(1); pp. 229-231.
Boye, E. and A. Lobner-Olesen Res Microbiol (1991) 142(2-3): pp. 131-135.
Brouillette, et al., Vaccine (2002) 20(17-18), pp. 2348-2357.
Brown, et al., FEBS Letter, (1980) 122(2), pp. 275-278.
Bulut, S., et al., Appl Environ Microbiol (1999) 65(10), pp. 4464-4469.
Chang, S., et al. N Engl J Med (2003) 348:14, pp. 1342-1347.
Chambers, et al., J Infect Dis (1990) 161(6), pp. 1170-1176.
Chambers, H. F., Clin Microbiol Rev (1997) 10(4), pp. 781-791.
Cohen, C. Y. and E. Sahar, J Clin Microbiol (1989) 27(6), pp. 1250-1256.
David, M. D., et al. J Hosp Infect (2006) 64(3), pp. 244-250.
Diaper, J. P., et al., Appl Microbiol Biotechnol (1992) 38(2), pp. 268-272.
Doern, G. V., et al., J Clin Microbiol (1994) 32(7), pp. 1757-1762.
Donovan, et al., FEMS Microbiol Lett (2006) 265(1), pp. 133-139.
Durodie, et al., Cytometry (1995) 21(4), pp. 374-377.
Eiff, et al., J Antimicrob Chemother (2008) 61(6): pp. 1277-1280.
Eigner, et al., J Clin Microbiol (2005) 43(8): pp. 3829-3834.
Fouchet, et al., Biol Cell (1993) 78(1-2): pp. 95-109.
Gant, et al., J Med Microbiol, (1993) 39(2): pp. 147-154.

(Continued)

*Primary Examiner* — Paul Zarek
*Assistant Examiner* — George W Kosturko
(74) *Attorney, Agent, or Firm* — Nixon Peabody LLP; Ronald I. Eisenstein; Leena H. Karttunen Contarino

(57) ABSTRACT

Described herein is a method and a device for expediting delivery of an agent to a damaged bacterial cell. In one embodiment, the methods and devices are useful for screening candidate antibiotics. In another embodiment, the methods and devices described herein are used to determine susceptibility of bacteria to an antibiotic. The methods also provide a method for determining an appropriate antibiotic to treat an individual having a bacterial infection.

16 Claims, 17 Drawing Sheets

(56) References Cited

OTHER PUBLICATIONS

Georgopapadakou, et al., Antimicrob Agents Chemother (1986) 29(2): pp. 333-336.
Ghuysen, et al., Trends Microbiol, (1994) 2(10): pp. 372-380.
Gilbert, et al., J. CMAJ (2006) 175(2): pp. 149-154.
Gosbell, et al., et al. Pathology (2006) 38(3): pp. 239-244.
Hartman, et al., J Bacteriol (1984) 158(2): pp. 513-516.
Huletsky, et al., J Clin Microbiol (2004) 42(5): pp. 1875-1884.
Jepras, et al., Appl Environ Microbiol (1995) 61(7): pp. 2696-2701.
Jones, et al. Manual of clinical microbiology, American Society for Microbiology, (1985), pp. 972-977.
Kaprelyants, et al., Kell Journal of Applied Bacteriology (1992) 72: pp. 410-422.
Kazakova, et al., N. Engl. J Med (2005) 352(5): pp. 468-475.
Langsrud, et al., J Appl Bacteriol (1996) 81(4): pp. 411-418.
Lloyd, et al., FEMS Microbiol Lett (1995) 133: pp. 1-7.
Martinez, et al., Cytometry (1982) 3(2): pp. 129-133.
Mascari, et al., Ann Biomed Eng (2001) 29(11): pp. 956-962.
Mascari, et al., Biotechnol Bioeng (2003) 83(1): pp. 65-74.
Mason, et al., J Appl Bacteriol (1995) 78(3): pp. 309-315.
Mason, et al., J Microsc, (1994) 176(Pt 1): pp. 8-16.
Mason, et al., J Antimicrob Chemother, (1995) 36(2): pp. 441-443.
Matsen, et al., Diagn Microbiol Infect Dis (1985) 3(6 Suppl):pp. 73S-78S.
McDougal, et al., J Clin Microbiol (2003) 41(11): pp. 5113-5120.
Metzger, et al., "Direct identification of methicillin resistant *Staphylococcus aureus* using small numbers of immobilized cells and response to oxacillin by automated growth analysis" (2007), C-032.
MMWR Morb Mortal Wkly Rep (2004) 53(15): pp. 322-333.
MMWR Morb Mortal Wkly Rep, (2002) 51(26), pp. 565-587.
O'Flaherty, et al., J Bacteriol (2005) 187(20): pp. 7161-7164.
Ordonez, et al., Cytometry (1993) 14(7): 811-818.
Pore, et al., J Antimicrob Chemother (1994) 34(5): pp. 613-627.
Roth, et al., Appl Environ Microbiol (1997) 63(6): pp. 2421-2431.
Sahoo, et al., Suraishkumar Biotechnol Bioeng (2006) 94(1): pp. 118-127.
Sahoo, et al., Biotechnol Prog (2003) 19(6): pp. 1689-1696.
Sellenriek, et al., 105th General Meeting of the American Society for Microbiology Atlanta, Ga, (2005) Abstact only.
International Search Report issued in PCT/US2010/033523 on Nov. 19, 2010.
Boedicker, et al., Lab on a Chip, vol. 8, 2008, pp. 1265-1272.
Johnson, et al, BMC Microbiology, vol. 6, No. 1, 2006, pp. 83-87.
Dominika Kulinski et al., Biomedical Microdevices, vol. 11, No. 3, 2009, pp. 671-678.
Gordon et al., International Journal of Systematic Bacteriology, vol. 27, No. 3, 1977, pp. 176-178.
Sakamoto et al., Applied and Environmental Microbiology, vol. 71, No. 2, 2005, pp. 1117-1121.
Schulze et al., Photonics, vol. 2, No. 4, 2009, pp. 199-211.
Roth et al., Applied and Environmental Microbiology, vol. 63, No. 6, 1997, pp. 2421-2431.
Metzger et al., 107th General meeting of the American Society for Microbiology (ASM), Poster C-032, 2007, Abstract only.

* cited by examiner

METHOD AND DEVICE FOR RAPID DETECTION OF BACTERIAL ANTIBIOTIC RESISTANCE/SUSCEPTIBILITY

CROSS REFERENCE TO RELATED APPLICATIONS

The present application is a continuation application under 35 U.S.C. §120 of an international application No. PCT/US2010/033523, filed on May 5, 2010, which claims the benefit under 35 U.S.C. §119(e) of U.S. Provisional Application No. 61/175,605, filed May 5, 2009, the contents of which are incorporated herein by reference in their entirety.

GOVERNMENT SUPPORT

This invention was made with Government support under Contract No. AI079474 awarded by the National Institutes of Health. The Government has certain rights in the invention.

BACKGROUND

Disease causing microbes that have become resistant to drug therapy are an increasing public health problem. Factors contributing to the rise in antibiotic resistance include widespread and inappropriate prescription of broad spectrum antibiotics and patient non-compliance to antibiotic regimens. The combination of these factors has resulted in some sobering statistics. For example, an estimated 70 percent of pathogenic bacteria in hospitals are resistant to at least one of the drugs most commonly used to treat infections (Federal Drug Administration (2007)). *Staphylococcus aureus*, a well known major cause of nosocomial infections, has recently taken on a new role in causing new cases of community-acquired infections in hosts without significant predisposing risk factors. The number of *S. aureus* infections and its resistance to a variety of antibiotics is increasing with 40%-60% of nosocomial *S. aureus* infections in the U.S. being methicillin-resistant and many being multi-drug resistant.

SUMMARY OF THE INVENTION

Described herein are rapid diagnostic methods and devices for determining antibiotic susceptibility of bacteria in a sample to enable physicians to accurately and rapidly treat bacterial pathogens. The diagnostic methods are based on the observation that the application of shear stress (and/or chemical stress) to bacteria in the presence of an antibiotic permits one to determine the sensitivity (or resistance) of a bacterium to the antibiotic without requiring a cell growth phase of the bacterium. Shear and/or chemical stress applied to bacteria catalyzes the biochemical pathways to repair damage to the cells. These pathways are the targets of antibiotics and therefore repair is inhibited in the presence of the antibiotic. In general, bacteria that are susceptible to such an antibiotic will die in the presence of a stressor, while resistant strains can repair the stress-induced damage. Thus, the susceptibility of the organism can be determined without waiting for bacterial growth.

The methods and devices described herein are also useful for rapid determination of an appropriate antibiotic useful for treating an infection in an individual.

In one aspect, the methods described herein relate to a method for expediting delivery of an agent comprising a reporter moiety to a damaged cell, the method comprising: (a) immobilizing bacteria to a solid support, (b) contacting said bacteria with an agent comprising a reporter moiety, (c) subjecting said immobilized bacteria to a stressor in the presence or absence of an antibiotic, and (d) detecting a signal from said reporter moiety, wherein if a signal is detected the agent has been delivered into the cell and wherein the signal is indicative of cell damage.

In one embodiment of this aspect and all other aspects described herein, detection is performed between 5 and 25 minutes from contacting the bacteria with the agent.

In another embodiment of this aspect and all other aspects described herein, the chemical stress comprises lysostaphin. In another embodiment, the chemical stress comprises lysozyme, an endolysin, oxidative stress or a porin.

In another embodiment of this aspect and all other aspects described herein, the physical stress comprises shear stress, osmotic stress, acidic pH or basic pH.

In another embodiment of this aspect and all other aspects described herein, the detecting step comprises detecting fluorescence emission from a fluorescent dye.

In another embodiment of this aspect and all other aspects described herein, the agent comprises a fluorescent dye.

In another embodiment of this aspect and all other aspects described herein, the fluorescent dye detects (e.g., stains) gram negative and/or gram positive bacteria.

In one embodiment, the fluorescent dye is non-toxic, taken up only by damaged cells, and/or has a high signal to noise ratio.

In another embodiment of this aspect and all other aspects described herein, the fluorescent dye is Sytox green or $DiBAC_4(3)$.

In another embodiment of this aspect and all other aspects described herein, the solid support comprises a glass slide.

In another embodiment of this aspect and all other aspects described herein, the glass slide is functionalized.

In another embodiment of this aspect and all other aspects described herein, the method is automated.

In another aspect, the methods and devices described herein relate to a device comprising a multiple channel flow cell, each channel of which comprises one wall decorated with immobilized bacteria. Trapped bacteria are exposed to shear stress by flowing fluid continuously across the bacterial surface. The fluid is a mixture of growth media and fluorescent dye with or without antibiotic. The fluorescent dye is chosen such that it only stains the cell if the membrane becomes permeabilized or the membrane potential changes indicating that the damaged cell is unable to recover in the presence of an antibiotic.

Provided herein in one aspect is a device for determining antibiotic sensitivity of bacteria, the device comprising: (a) two solid supports separated by a gasket, wherein a channel or a plurality of channels is formed between the two solid supports, (b) a metal housing comprising an inlet and outlet opening; and (c) a pump.

In one embodiment of this aspect and all other aspects described herein, each channel is filled with a different antibiotic.

In another embodiment of this aspect and all other aspects described herein, each channel is filled with an agent comprising a reporter moiety that preferentially binds to damaged bacteria.

In one embodiment of this aspect and all other aspects described herein, the solid support comprises a glass slide or a plastic (e.g., polystyrene) surface.

In another embodiment of this aspect and all other aspects described herein, the gasket comprises silicone rubber.

In another embodiment of this aspect and all other aspects described herein, one of the two solid supports is functionalized to permit immobilization of a bacterial cell.

In another embodiment of this aspect and all other aspects described herein, the device further comprises immobilized bacterial cells.

In another embodiment of this aspect and all other aspects described herein, the channel is 50-900 µm wide.

In another embodiment of this aspect and all other aspects described herein, the pump comprises a syringe pump.

In another embodiment of this aspect and all other aspects described herein, the device further comprises (a) tubing that connects the pump to the inlet opening and permits fluid to be pumped into the inlet opening from the pump; and (b) tubing that connects the outlet opening to the pump and permits fluid to be returned to the pump from the outlet opening.

In another embodiment of this aspect and all other aspects described herein, the metal housing can be integrated into a microscope stage.

In another embodiment of this aspect and all other aspects described herein, the device further comprises a microscope.

In another embodiment of this aspect and all other aspects described herein, the device further comprises a camera.

The device of claim 1, further comprising a plurality of channels.

Also described herein is a device for determining antibiotic sensitivity of bacteria as shown in FIG. 2A.

In another aspect, provided herein is a method for determining sensitivity of bacteria to an antibiotic, the method comprising: (a) immobilizing bacteria to a solid support, (b) contacting said bacteria with an agent comprising a reporter moiety, which preferentially binds to damaged bacterial cells, (c) subjecting said immobilized bacteria to a stressor in the presence or absence of an antibiotic, (d) detecting a signal from said reporter moiety, wherein detection of said signal indicates that said bacteria are susceptible to said antibiotic, and wherein a lack of signal indicates that said bacteria are resistant to said antibiotic.

In one embodiment of this aspect and all other aspects described herein, the stressor comprises physical and/or chemical stress.

Also provided herein is a method for treating an individual having a bacterial infection, the method comprising: (a) immobilizing bacteria obtained from a biological sample from said individual to a solid support, (b) contacting said bacteria with an agent comprising a reporter moiety, which preferentially binds to damaged bacterial cells, (c) subjecting said immobilized bacteria to a stressor in the presence of an antibiotic, (d) detecting a signal from said reporter moiety, wherein detection of said signal indicates that said bacteria are susceptible to said antibiotic, and (e) administering said antibiotic to said individual, thereby treating said bacterial infection.

In one embodiment of this aspect and all other aspects described herein, the stressor comprises physical and/or chemical stress.

In another embodiment of this aspect and all other aspects described herein, the method comprises subjecting the bacteria to a panel of at least two different antibiotics.

In another embodiment of this aspect and all other aspects described herein, the chemical stress comprises lysostaphin, lysosyme, an endolysin, oxidative stress or a porin.

In another embodiment of this aspect and all other aspects described herein, the physical stress comprises shear stress, osmotic stress, acidic pH or basic pH.

In another embodiment of this aspect and all other aspects described herein, the detecting step comprises detecting fluorescence.

In another embodiment of this aspect and all other aspects described herein, the agent comprises a fluorescent dye.

In another embodiment of this aspect and all other aspects described herein, the fluorescent dye detects (e.g., stains) gram negative and/or gram positive bacteria.

In another embodiment of this aspect and all other aspects described herein, the fluorescent dye is Sytox green or $DiBAC_4(3)$.

In another embodiment of this aspect and all other aspects described herein, the solid support comprises a glass slide.

In another embodiment of this aspect and all other aspects described herein, the glass slide is functionalized.

In another embodiment of this aspect and all other aspects described herein, the method comprises a high-throughput method.

Also described herein is a machine for obtaining data regarding response of bacteria to an antibiotic in a biological sample from a subject comprising: (a) a flow chamber assay device comprising immobilized bacterial cells from a biological sample and a plurality of channels that permit contact with one or more antibiotics or mixtures thereof, and additionally allowing for a stressor to be added to the bacterial cells; (b) a determination system configured to detect entry of a test agent comprising a detectable moiety into the immobilized bacterial cells upon presence of a stressor; (c) a storage device configured to store data output from the determination system; (d) a comparison module adapted to compare the data stored on the storage device with reference and/or control data and optionally further adapted to compare the intensity of a signal from the detectable moiety among the plurality of channels, and (e) a display module for displaying a page of retrieved content for the user on a client computer, wherein (i) the retrieved content for each channel is detection of the presence of the detectable moiety in the bacterial cell in the presence of an antibiotic and the signal is that the cell is susceptible to the antibiotic, and/or (ii) the retrieved content for each channel is the absence of the detectable moiety in the bacterial cell in the presence of an antibiotic and the signal is that the cell is resistant to the antibiotic, and/or (iii) the retrieved content for each channel is a signal intensity of the detectable moiety in the presence of an antibiotic among the plurality of channels, wherein the highest intensity detected among a plurality of different channels of the device, produces a signal that the antibiotic is preferred for treatment of a bacterial infection comprising the bacterial cells compared to any of the other channels, wherein a lower signal intensity is detected.

In one embodiment of this aspect and all other aspects described herein, the control data comprises data from a channel in the device that is not treated with an antibiotic.

In another embodiment of this aspect and all other aspects described herein, the determination system is configured to detect fluorescence emission data.

Also described herein is a computer system for obtaining data regarding a biological specimen comprising: (a) a determination system configured to receive detection information, wherein the detection information comprises intensity of a signal from an agent comprising a detectable moiety upon entry into an immobilized bacterial cell in the presence of a stressor; (b) a storage device configured to store data output from the determination system; (c) a comparison module adapted to compare the data stored on the storage device with reference and/or control data, and to provide a retrieved content, and (d) a display module for displaying a page of the retrieved content for the user, wherein the retrieved content indicates that a bacterial cell (i) is susceptible to an antibiotic, (ii) is resistant to an antibiotic, and/or (iii) is a preferred antibiotic for treatment of a bacterial infection comprising the bacterial cells.

Another aspect described herein relates to a computer readable medium having computer readable instructions recorded thereon to define software modules including a determination system and a comparison module for implementing a method on a computer to determine a preferred antibiotic for treatment of a bacterial infection, the method comprising: (a) storing data about detection information representing entry of an agent comprising a reporter moiety into an immobilized and stressed bacterial cell or population of cells taken from a subject with a bacterial infection, wherein the detection information comprises the intensity of a signal from the agent comprising a detectable moiety upon entry into the immobilized and stressed bacterial cell; (b) comparing with the comparison module the data stored on the storage device with reference and/or control data, and to provide a retrieved content, and (c) displaying the retrieved content for the user, wherein the absence of entry of the agent into the bacterial cell indicates that the immobilized and stressed bacterial cell is resistant to the antibiotic, wherein the presence of the agent in the bacterial cell indicates that the immobilized and stressed bacterial cell is susceptible to the antibiotic, and wherein the antibiotic having the highest intensity of signal from the reporter moiety in the population of cells indicates that the antibiotic is the preferred antibiotic for treatment of a subject having the bacterial infection comprising the bacterial cells.

Also provided herein is a method for screening a candidate antibiotic for activity against a bacterial strain, the method comprising: (a) immobilizing bacteria to a solid support, (b) contacting said bacteria with an agent comprising a reporter moiety, which preferentially binds to damaged bacterial cells, (c) subjecting said immobilized bacteria to a stressor in the presence or absence of an effective amount of a candidate antibiotic, (d) detecting a signal from said reporter moiety, wherein detection of the signal indicates that the candidate antibiotic has activity against the bacterial strain, and wherein lack of signal indicates that the candidate antibiotic has no activity against the bacterial strain.

BRIEF DESCRIPTION OF THE FIGURES

FIG. 2B shows a system for use with a flow cell comprising a fluorescent microscope, wherein 200 is an inverted fluorescence and phase contrast microscope, 300 is a syringe side (upstream) tubing, 400 is stage/shutter controller, 500 is a 60 ml exelint syringe, 600 is a KDS 230 syringe pump, 700 is an X/Y-stage, 800 is an Z-axis stepper motor, 900 is a vibration isolated table (workstation) TE-CCD camera, 1000 denotes fluorescent excitation, 1100 is a waste bottle, and 1200 is a waste side (downstream) tubing. 2000 denoted an automatic image acquisition with XYZ-stage, shutter and pump control.

DETAILED DESCRIPTION

Figure 1:
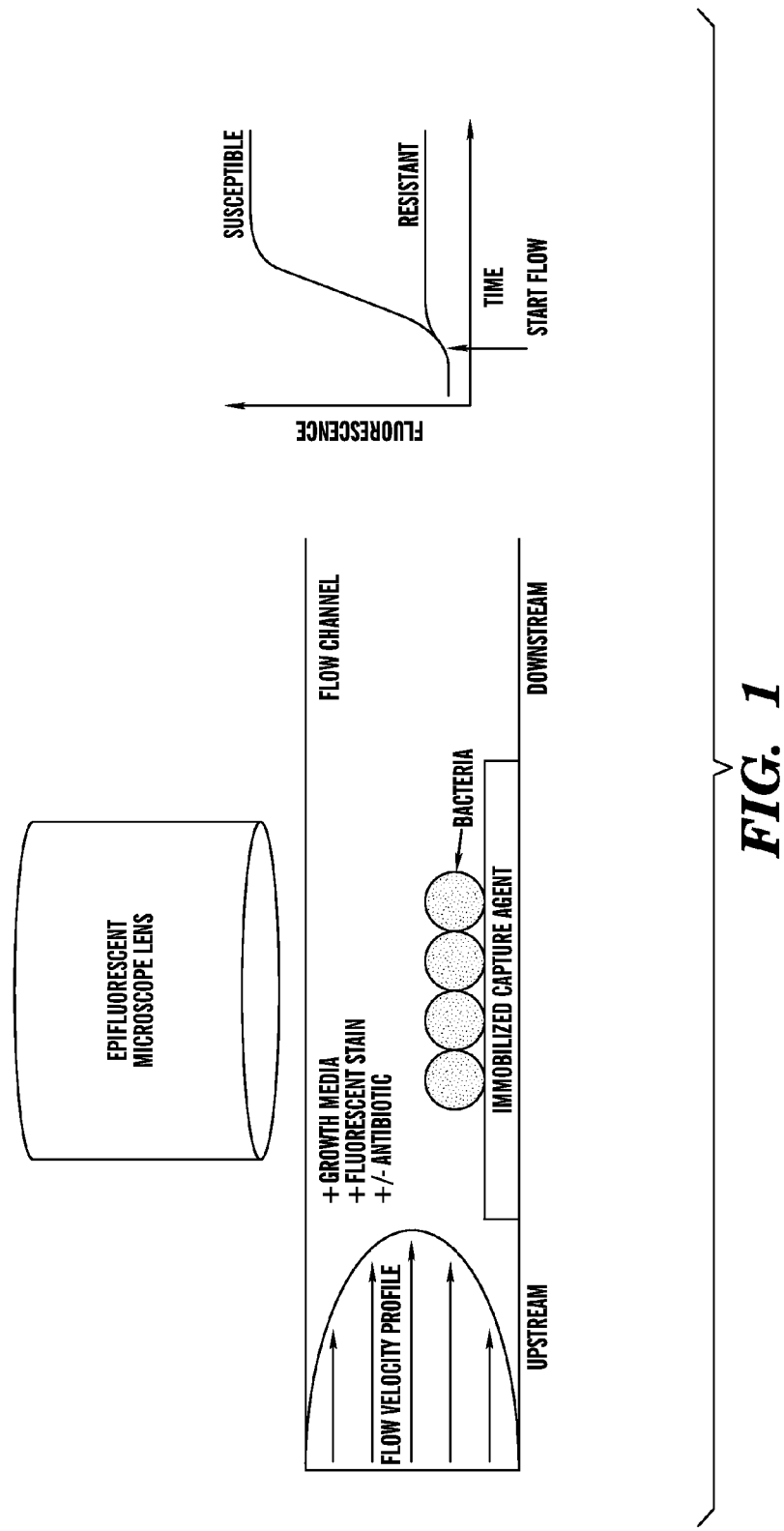
FIG. 1 shows a schematic diagram depicting a functional set-up of a device as described herein (left) and a graph depicting fluorescence measurements over time for antibiotic resistant and antibiotic susceptible bacterial strains (right).
Figure 2A:
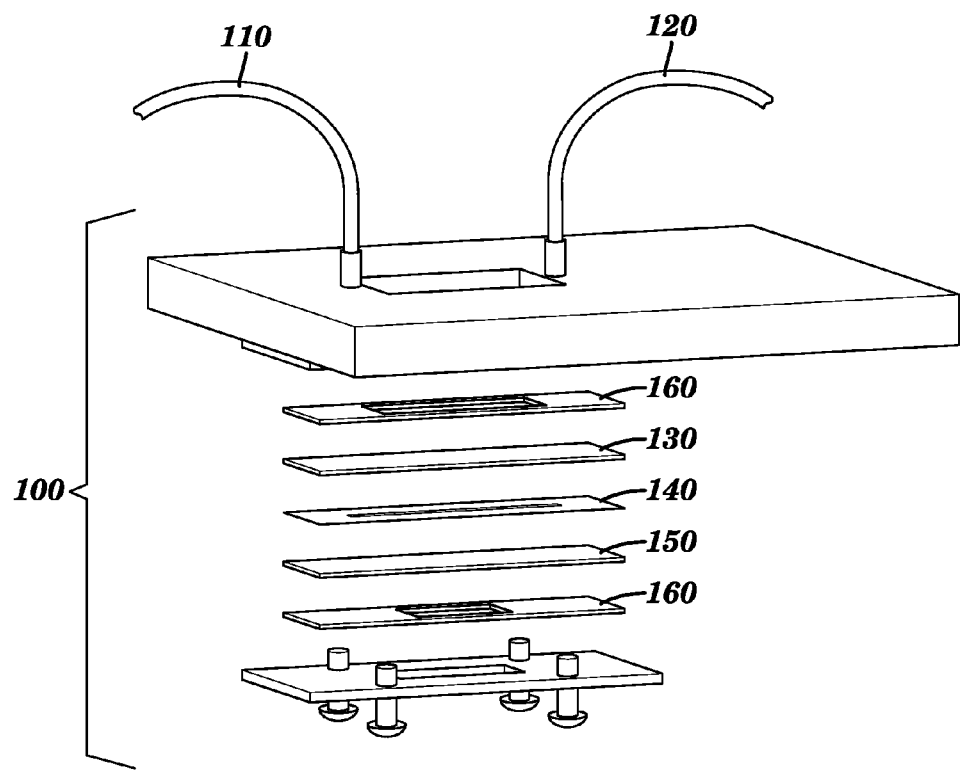
FIGS. 2A-2B show an exploded view of a flow cell (100) including a flow cell housing designed to insert into a fluorescent microscope stage (2A), wherein 110 is an inlet, 120 is an outlet, 130 is a glass slide with inlet/outlet, 140 is a silicone channel, 150 is a class slide with epoxide coating and 160 is a silicone padding.
Figure 2B:
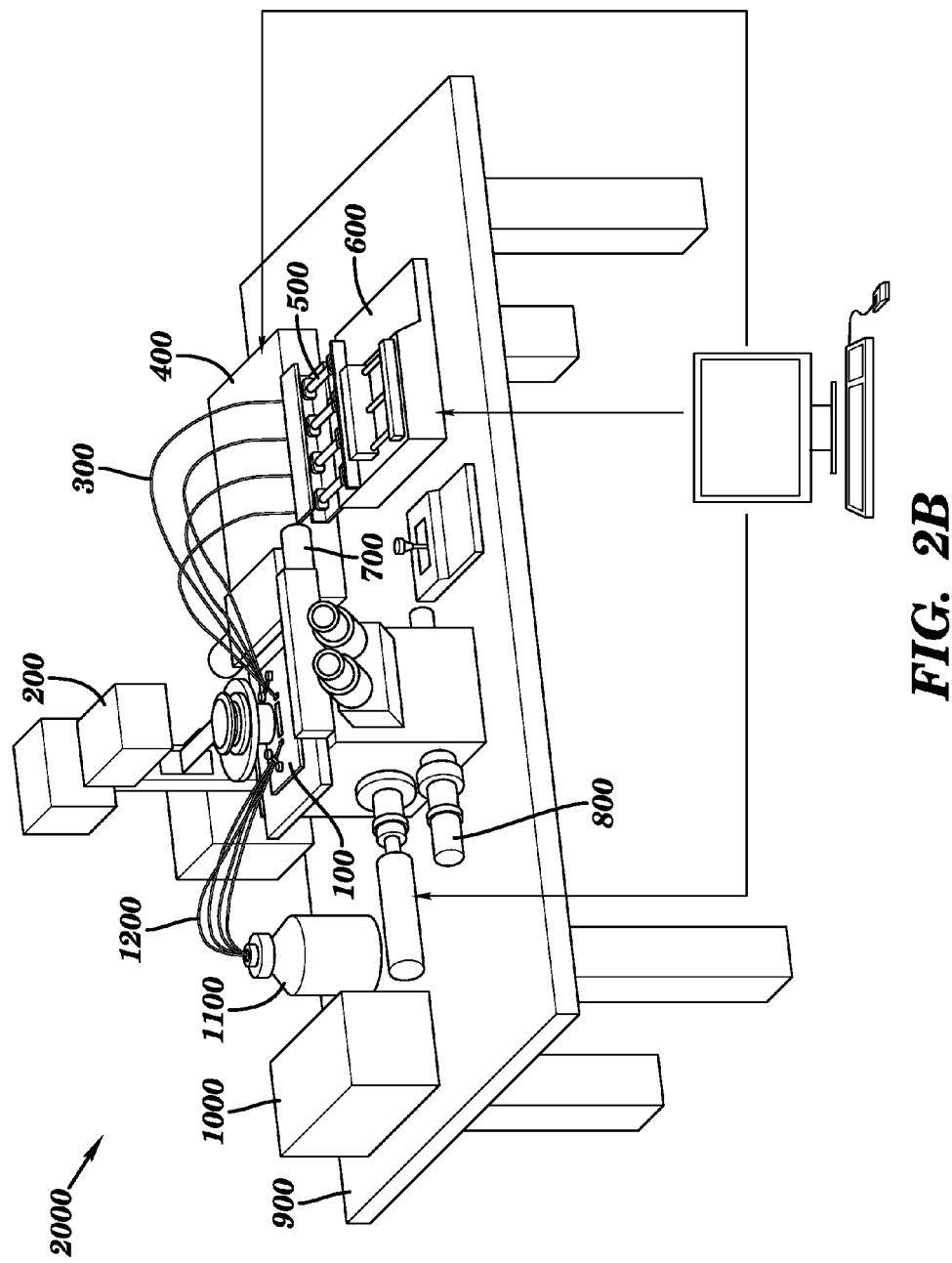
Figure 3:
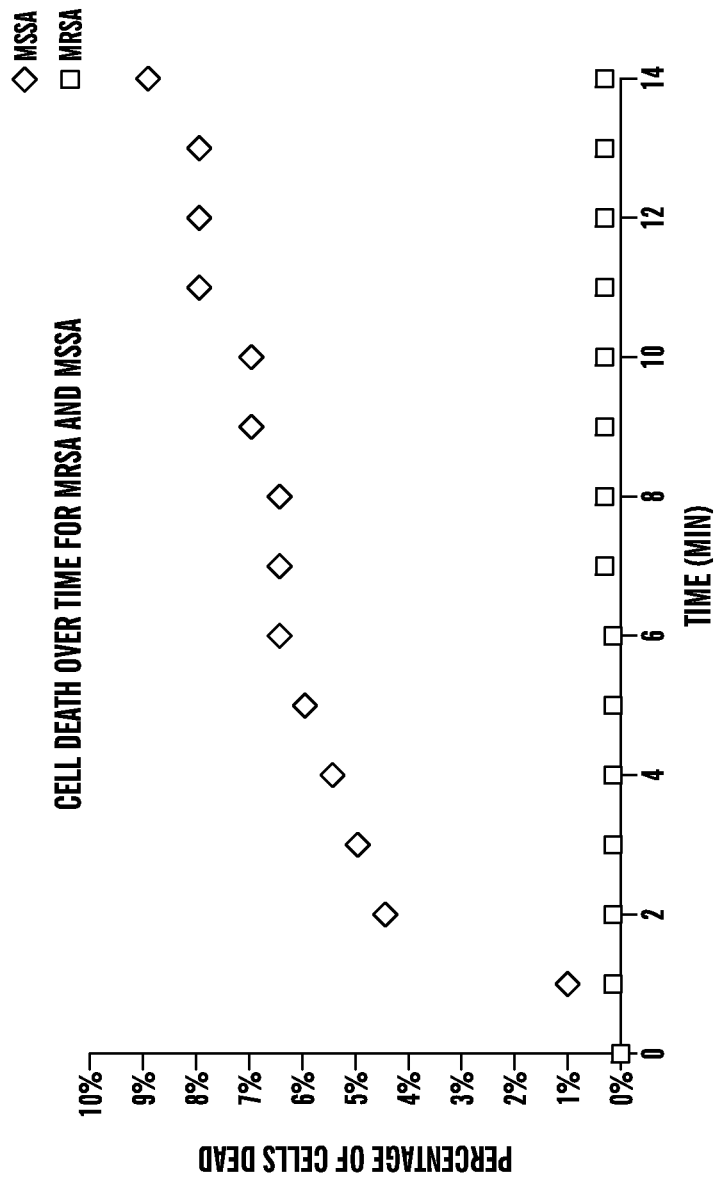
FIG. 3 shows a graph depicting cell death over time for methicillin-resistant S. aureus (MRSA) and methicillin-sensitive S. aureus (MSSA) during and following exposure to 10 µg/mL oxacillin, 0.6 ng/mL lysostaphin, and ~4200 s$^{-1}$ shear.
Figure 4:
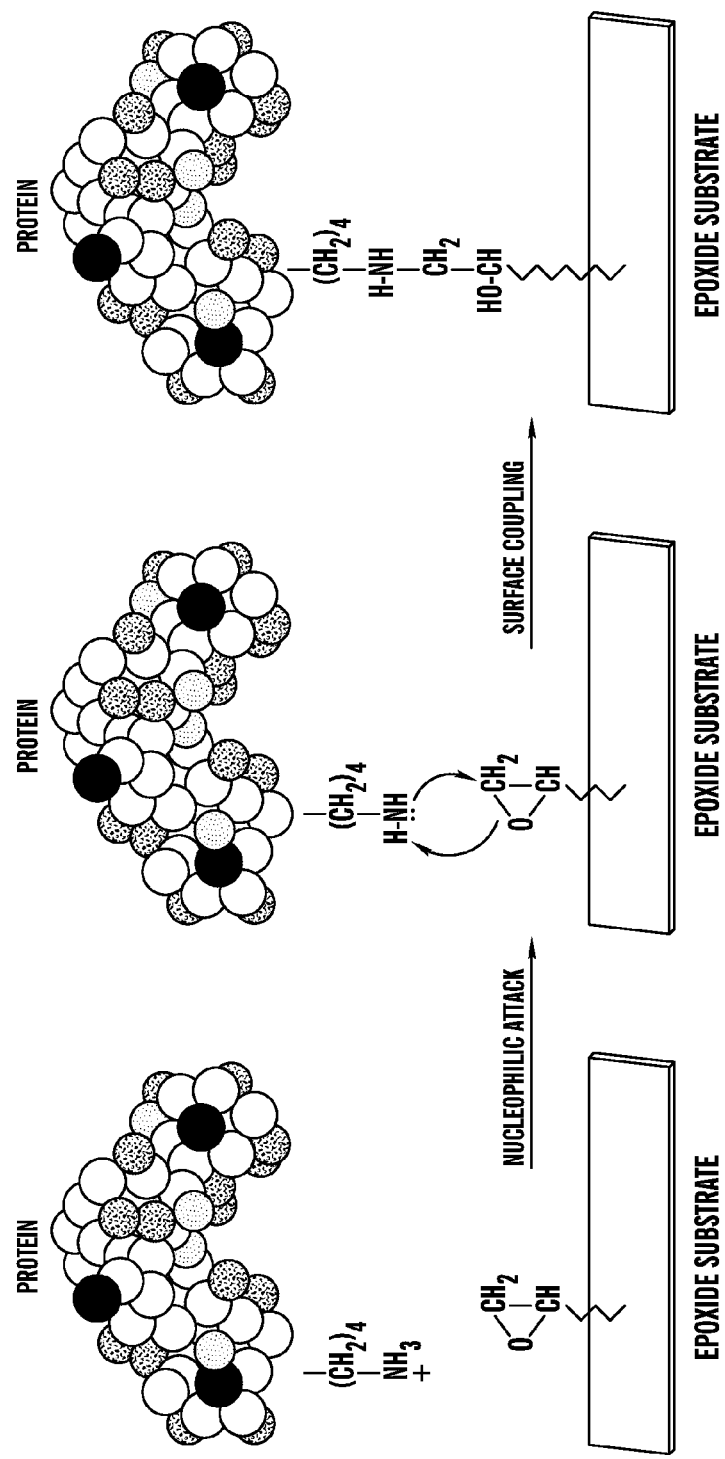
FIG. 4 shows an exemplary reaction for covalent attachment of a bacterium to epoxide glass substrates, where the proteins are organic molecules on the bacterium's surface.

Described herein are devices and methods to enable clinicians to prescribe targeted antibiotic therapy immediately, instead of the current practice of prescribing a broad-spectrum antibiotic initially and changing to targeted therapies when the antibiotic susceptibility profile is established. The method can be integrated with a rapid isolation technique for directly testing susceptibility of clinical specimens, such as by using immunomagnetic beads.

Current methods for detecting antibiotic susceptibility are based on the ability of bacteria to proliferate in the presence of antibiotics, and thus these techniques are time-consuming, costly, and insensitive, particularly for the evaluation of slow-growing organisms. Described herein are methods and devices useful as a rapid susceptibility test, which circumvents the need for a bacterial growth phase. Described herein are methods to detect the response of small numbers of cells to antibiotics in the presence of mechanical and/or chemical stressors to obviate the time needed for growth. In general, by straining the cell, the bacterium is challenged to repair itself. The repair processes of bacterial cells are often targets of antibiotics. If that repair process is hindered by an antibiotic, the cell will die or depolarize, which can be monitored via e.g., fluorescence stains. This methodology offers advantages over the current techniques by providing phenotypic information in an ultra-rapid time frame (e.g., 5-30 minutes) allowing physicians to make appropriate antibiotic treatment choices sooner.

Provided herein, in one aspect, is a device for measuring antibiotic resistance/susceptibility to an antibiotic. In one embodiment, a device (e.g., detection system) as described herein comprises a flow cell or a multiple channel flow cell, wherein the channel or the plurality of channels has one wall decorated with immobilized bacteria. Trapped bacteria are exposed to shear stress by flowing fluid continuously across the bacterial surface. The fluid is a mixture of growth media and a reporter stain (e.g., a fluorescent dye) with or without antibiotic. The reporter stain is chosen such that it only stains the cell if the membrane becomes permeabilized or the membrane potential changes indicating that the antibiotic has damaged the cell. The methods and devices described herein can be multiplexed either using multiple antibiotics or multiple organisms by the addition of more fluidic channels. In addition, the device provides a unique platform for rapid screening of candidate antibiotics from e.g., a library of small molecules. The methods and devices described herein can also be used to determine a minimum inhibitory concentration of an antibiotic with a particular strain of bacteria. The device and method can be integrated with current bacterial identification methodologies (e.g. culture post testing).

DEFINITIONS

As used herein, the phrases "antibiotic sensitivity of bacteria" or "sensitivity of bacteria to an antibiotic" reflects the ability of a particular antibiotic to prevent repair and/or promote damage to a bacterial cell. The "antibiotic sensitivity" of a bacterium can be assessed by measuring the degree of stressor-induced bacterial cell damage in the presence of an antibiotic; for example, cell damage can assessed by measuring the degree of fluorescence emitted from a fluorescent dye that detects damaged bacterial cells.

As used herein the terms "reporter stain," "agent comprising a reporter moiety" and "agent comprising a detectable moiety" are used interchangeably and refer to a molecule that accumulates differentially in damaged cells and undamaged cells, and further comprises a moiety that can be used for detection. For example, an "agent comprising a reporter moiety" encompasses a fluorescent dye that is taken up preferentially by damaged cells, while it is excluded and/or extruded by undamaged or repaired cells.

As used herein, the term "reporter moiety" or "detectable moiety" refers to a molecule, or moiety of a molecule, capable of producing a detectable signal such as e.g., fluorescence, chemiluminescence, a colorimetric signal etc.

A bacterium is considered to be "resistant" or "insensitive" to an antibiotic if the bacterium recovers from stressor-induced cell damage in the presence of an antibiotic to a substantially similar degree to that observed in an identical bacterial strain cultured in the absence of the antibiotic; that is a detectable signal of resistant cells in the presence of an antibiotic (e.g., fluorescent emission) is substantially similar to that of cells not treated with an antibiotic. Resistance to an antibiotic can be assessed using the methods described herein by e.g., a lack of fluorescence emission from a fluorescent dye that preferentially binds to damaged bacterial cells.

A bacterium is considered to be "susceptible" or "sensitive" to an antibiotic if the bacterium does not recover or is delayed from recovering from stressor-induced cell damage in the presence of an antibiotic. A bacterium is considered susceptible if e.g., fluorescence emission from a fluorescent dye that accumulates in dying cells is at least 10% higher than the fluorescence detected from the same bacterium in the absence of an antibiotic; preferably the fluorescence is at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10-fold higher, at least 100-fold higher, at least 1000-fold higher, at least 10000-fold higher or more than the fluorescence detected in the absence of an antibiotic. It is contemplated herein that a bacterium is susceptible for more than one antibiotic tested concurrently, thus the antibiotic that produces the highest intensity of fluorescence in a population of cells (indicating the highest level of cell death) is contemplated for use in treatment of an individual.

As used herein the term "stressor" refers to a physical/mechanical (e.g., shear stress) or chemical stress (e.g., lysostaphin, osmotic stress, pH, oxidative stress, enzymatic stress (e.g., lysozyme, endolysins), etc) that induces cell damage to an immobilized bacterium. The stressor should be strong enough to permit visualization of cell damage, for example by detecting fluorescence emission from a fluorescent dye that accumulates in dying cells as described herein, but should not be so strong as to induce substantial cell death in the absence of an antibiotic. The stressor should permit recovery of at least 60% of bacterial cells in the absence of an antibiotic in the culture conditions; preferably a recovery of at least 70%, at least 80%, at least 90%, at least 95%, at least 99% or even a recovery of 100% (i.e., total recovery) is achieved in the absence of an antibiotic over the time course of the methods described herein.

As used herein, the term "cell damage" is used to refer to any cell damage that can be differentially detected using an agent comprising a reporter molecule (e.g., a fluorescence agent that detects damaged cells). The term "cell damage" encompasses a non-lethal and repairable loss of e.g., bacterial cell wall integrity, such that the cell wall permits the cellular entry of a detectable agent (e.g., fluorescent dye) that is normally excluded (or vice versa). "Cell damage" can also be assessed functionally by the activation of cellular repair enzymes, such as those that promote peptidoglycan synthesis. The term "cell damage" is not intended to encompass damage that results in substantial bacterial cell death (e.g., greater than 40% cell death).

As used herein the terms "functionalization", or "functionalized" are used to describe modifications to a solid support, which permit or enhance immobilization of a bacterium. Functionalization of a solid support can encompass, for example attaching a protein, a polymer, a linker, a particle, a chemical group, or a combination thereof to the solid support. Some non-limiting examples of agents useful for functionalization include fibronectin, fibrinogen, gelatin, collagen, epoxide-activation, elastin, among others. It is preferred that the functionalization permits binding of a variety of bacterial species and/or strains, i.e., not specific to a particular bacterial strain.

As used herein, the term "high throughput" refers to a device/system or a method for determining antibiotic resistance/susceptibility from at least two samples simultaneously, iteratively, concurrently, or consecutively. In one embodiment the number of samples assayed simultaneously is in the range of 1-10000 samples inclusively; in alternate embodiments the following ranges of sample number can be assayed in the high throughput device or system: 1-5000 samples inclusive, 1-2500, 1-1250, 1-1000, 1-500, 1-250, 1-100, 1-50, 1-25, 1-10, 1-5, 7500-10000, 5000-10000, 4000-10000, 3000-10000, 2000-10000, 1000-10000, 500-10000, 100-1000, 200-1000, 300-1000, 400-1000, 500-1000, inclusive. The term "high-throughput" encompasses automation of the methods described herein using e.g., robotic pippettors, robotic samplers, robotic shakers, data processing and control software, liquid handling devices, incubators, detectors, hand-held detectors etc. For the purposes of automation, it may be preferred that the number of samples tested at one time correspond to the number of wells in a standard plate (e.g. 6-well plate, 12-well plate, 96-well plate, 384-well plate, etc.). The samples can be obtained from a plurality of individuals, or from a plurality of samples obtained from a single individual. A high-throughput system permits one to test susceptibility of a bacterial strain to multiple antibiotics simultaneously, to test for susceptibility to a particular antibiotic in a plurality of samples, or to test multiple doses of the same antibiotic in a sample.

As used herein the phrase "panel of at least two different antibiotics" refers to a plurality of different antibiotic compounds assessed at approximately the same time. A "plurality" refers to at least 2 different antibiotics; preferably the plurality is in the range of 2-100 different antibiotics, other preferred ranges include 2-90, 2-80, 2-70, 2-60, 2-50, 2-40, 2-30, 2-20, 2-12, 2-10, 2-6, 2-5, 10-50, 10-40, 10-30, 10-20, 12-24, 12-36, 12-48, 12-60, 12-72, 25-50, 25-60, 25-70, 50-100, 60-100, 70-100, 80-100, 90-100, among others.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Bacteria

Essentially any bacteria can be tested for antibiotic susceptibility or used in screening a candidate antibiotic using the methods and devices described herein. Particularly relevant bacteria include pathogenic bacteria that infect mammalian hosts (e.g., bovine, murine, equine, primate, feline, canine, and human hosts). In one embodiment, the bacteria is one that infects and/or causes disease in a human host. Examples of pathogenic bacteria include e.g., members of a bacterial species such as *Bacteroides, Clostridium, Streptococcus, Staphylococcus, Pseudomonas, Haemophilus, Legionella, Mycobacterium, Escherichia, Salmonella, Shigella, Vibrio*, or *Listeria*.

Some clinically relevant examples of pathogenic bacteria that cause disease in a human host include, but are not limited to, *Bacillus anthracis, Bordetella pertussis, Borrelia burgdorferi, Brucella aborus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtheriae, Enterococcus faecalis,* vancomycin-resistant *Enterococcus faecalis, Enterococcus faecium, Escherichia coli,* enterotoxigenic *Escherichia coli* (ETEC), enteropathogenic *Escherichia coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermis, Staphylococcus saprophyticus,* methicillin-resistant *Staphylococcus aureus* (MRSA), vancomycin-resistant *Staphylococcus aureus* (VSA), *Streptococcus agalactiae, Streptococcus pneumoniae, Streptococcus pyogenes, Treponema pallidum, Vibrio cholerae,* and *Yersinia pestis*.

Solid Supports

In one embodiment of the present invention, a bacterium is immobilized to a solid substrate. Immobilization of a bacterium permits generation of a mechanical shear stress by flowing liquid over the bacterium. In its simplest version, a solid support comprises a glass slide to which the bacterium binds. In other embodiments of the invention, the bacterium is anchored to a solid support, which can comprise for example, a magnetic particle, polymeric microsphere, filter material, or the like, which permits the generation of mechanical shear stress.

A variety of other solid substrates can be used, including, without limitation, the following: cellulose; nitrocellulose; nylon membranes; papers, fiberglass, fabrics made of synthetic materials, glass beads; polystyrene matrices; activated dextran; coated polystyrene beads; agarose; polyethylene; functionalized plastic, glass, silicon, aluminum, steel, iron, copper, nickel, and gold; tubes; wells; microtiter plates or wells; slides; discs; columns; beads; membranes; well strips; films; chips; and composites thereof. In one embodiment, a portion of the surface of a solid substrate is coated with a chemically functional group to allow for binding of the bacterium to the surface of the solid substrate. Solid substrates with the functional group already included on the surface can be obtained from commercial sources. In addition, the functional groups may be added to the solid substrates by the practitioner.

If a solid substrate is made of a polymer, it can be produced from, without limitation, any of the following monomers: acrylic acid; methacrylic acid; vinylacetic acid; 4-vinylbenzoic acid; itaconic acid; allyl amine; allylethylamine; 4-aminostyrene; 2-aminoethyl methacrylate; acryloyl chloride; methacryloyl chloride; chlorostyrene; dischlorostyrene; 4-hydroxystyrene; hydroxymethyl styrene; vinylbenzyl alcohol; allyl alcohol; 2-hydroxyethyl methacrylate; poly(ethylene glycol) methacrylate; and mixtures thereof, together with one of the following monomers: acrylic acid; acrylamide; methacrylic acid; vinylacetic acid; 4-vinylbenzoic acid, itaconic acid; allyl amine; allylethylamine; 4-aminostyrene; 2-aminoethyl methacrylate; acryloyl chloride; methacryloyl chloride; chlorostyrene; dichlorostyrene; 4-hydroxystyrene; hydroxymethyl styrene; vinylbenzyl alcohol; allyl alcohol; 2-hydroxyethyl methacrylate; poly(ethylene glycol)methacrylate; methyl acrylate; methyl methacrylate; ethyl acrylate; ethyl methacrylate; styrene; 1-vinylimidazole; 2-vinylpyridine; 4-vinylpyridine; divinylbenzene; ethylene glycol dimethacrylate; N,N'-methylenediacrylamide; N,N'-phenylenediacrylamide; 3,5-bis(acryloylamido)benzoic acid; pentaerythritol triacrylate; trimethylolpropane trimethacrylate; pentaerythritol tetraacrylate; trimethylolpropane ethoxylate (14/3 EO/OH) triacrylate; trimethylolpropane ethoxylate (7/3 EO/OH) triacrylate; trimethylolpropane propoxylate (1 PO/OH) triacrylate; trimethylolpropane propoxylate (2 PO/OH) triacrylate; and mixtures thereof.

In one embodiment, bacterial cells are immobilized on a porous solid support. The terms "porous" or "porosity" generally refers to materials having a distribution of pore sizes ranging from 100 nm to 1000 μm. Particularly useful inorganic fibers and fibrous material compositions are natural and synthetic fibers made from glass, ceramic, metal, quartz, silica, silicon, silicate, silicide, silicon carbide, silicon nitride, alumina, aluminate, aluminide, carbon, graphite, boron, borate, boride, and boron nitride. Particularly useful natural or synthetic fibers and fibrous material compositions are polymer fibers made from aromatic polyamides, nylons, polyarylonitrile, polyesters, olefins, acrylics, cellulose, acetates, anidex, aramids, azlon, alatoesters, lyocell, spandex, melamines, modacrylic, nitrile, polybenzinidazole, polypropylene, rayons, lyorell, sarans, vinyon, triacetate, vinyl, rayon, carbon pitch, epoxies, silicones, sol gels, polyphenylene-benzobis-ozazole, polyphenylene sulfides, polytetrafluoroethylene, teflon, and low density or high density polyethylene. In one embodiment, the porous solid support comprises an acid-washed silk screen.

It is preferred that a solid support permits immobilization of a wide variety of bacterial species and/or strains in a non-specific manner. This can be achieved, for example, by using species non-specific reactive chemistries (e.g., epoxides) to functionalize the solid support. The solid support should not induce death of the cells nor should it interfere with normal cellular processes (e.g., cell wall production/repair, metabolism, energy production etc.).

Bacterial Immobilization

To ensure that a bacterial cell immobilization technique can be applied to many cell types, bacteria can be immobilized using a technique similar to that used for protein and DNA immobilization the field of microarrays. Bacterial cells can be covalently linked to glass slides using chemically activated slides as the substrate (e.g. ARRAYIT® Superepoxy 2 slides, available for ARRAYIT®, Sunnyvale, Calif.). Bacteria, such as *staphylococcus*, can be immobilized by adherence to epoxide-activated slides. Primary amines on the bacterial cell wall surface act as nucleophiles, attacking epoxy groups and coupling the protein covalently to the surface. Bacteria can be immobilized on a surface (e.g., a glass slide) using any reactive chemistry that permits immobilization of any bacterial cell in a species non-specific manner.

To optimize the immobilization protocol to reproducibly bind live cells to the glass slide surface at a density that enables appropriate quantification, the number of bacteria bound to the surface can be counted under an optical microscope. To ease visualization, the cells can be stained with a fluorescent dye such as LIVE (Molecular Probes).

Alternatively, immobilization of the bacteria can be performed via bacterial adhesins. Capture agents useful for immobilizing bacteria can include those to which the bacteria bind in vivo for attachment to host tissue (e.g., fibronectin, elastin, fibrinogen etc). Additionally, to have broad strain sensitivities, the adhesins for the capture agents should be highly conserved.

Shear Stress

Shear stress, in the presence or absence of chemical stress, applied to bacteria will significantly reduce the time required to observe the effects of antibiotics on cells. This is due, in part, to the ability of bacteria to respond to their environment and adapt to stress by activating various biochemical pathways to cope with the stressors and changes in environment. Shear forces can be applied to induce stress on bacteria and has been shown to cause responses in various bacterial model systems, (e.g., *Bacillus subtilis* (Sahoo, S., K. K. Rao, and G. K. Suraishkumar *Biotechnol Bioeng* (2006) 94(1):118-27; Sahoo, S., et al., *Biotechnol Prog* (2003) 19(6):1689-96), *Microbacterium lacticum* (Bulut, S., et al., *Appl Environ Microbiol* (1999) 65(10):4464-9), *Bacillus thuringiensis* (Wu, W. T., et al., *Appl Microbiol Biotechnol* (2002) 58(2): 175-7), and *Escherichia coli* (Thomas, W. E., et al., *Cell* (2002) 109(7):913-23)). If the shear rates are high (greater than 2000 $s^{-1}$) or exerted over an extended period of time (hrs), shear forces can lead to cell death (Sahoo, S., et al., *Biotechnol Bioeng* (2006) 94(1):118-27; Sahoo, S., et al., *Biotechnol Prog* (2003) 19(6):1689-96; Bulut, S., et al., *Appl Environ Microbiol* (1999) 65(10):4464-9). More moderate shear rates can cause down-regulation of protein secretions, as in the case of *Bacillus thuringiensis* (Wu, W. T., et al., *Appl Microbiol Biotechnol* (2002) 58(2):175-7). Interestingly, in some pathogens, bacterial adhesion to target cells can increase in the presence of increased shear stress (Thomas, W. E., et al., *Cell* (2002) 109(7):913-23). These examples of bacterial responses to shear stress indicate that shear stress can induce bacteria to activate biochemical pathways.

It is contemplated herein that a sufficient shear force needs to be applied to stress the cells, without causing the bacteria to be sheared off of the immobilized capture agent and then out of optical view. Additionally, at the high shear extreme, a danger exists of outright killing the cells. It is well within the skill of one in the art and/or using methods described herein to identify an appropriate level of shear stress for use with the methods and devices described herein by monitoring cell damage induced by a stressor and the degree of recovery of bacterial cells in the absence of an antibiotic.

The amount of shear stress can be optimized for a particular bacterium by altering the rate or velocity of flow across the immobilized bacteria. It is contemplated herein that different strains or species of bacteria will have different responses to a shear stress. One of skill in the art can easily optimize the amount of shear stress necessary for the methods described herein, for example, by increasing or decreasing the flow velocity across cells in one or more channels and comparing the level of e.g., fluorescence to that detected in a control channel having a fixed flow velocity. In one embodiment, the methods and devices described herein permit the shear stress to be modified using e.g., a pump or multiple pumps to control the flow velocity.

The flow rate and velocity needed to induce the shear stress is dependent on the geometry and size of the channel. Shear stress can be calculated using the formula:

$$\text{shear stress} = (6*Q)/(w*h^2) \quad \text{(Formula I)}$$

wherein Q is the flow rate, w is the width and h is the height of the channel of the flow cell through which the medium is pumped. In the exemplary device described herein in the Examples section, flow rates typically range between 0.5-5 mL/min, e.g., between 0.5-4 mL/min, 0.5-3 mL/min, 0.5-2 mL/min, 0.5-1 mL/min, 0.5-0.75 mL/min, etc. Table 1 shows sample calculations of shear stress for different rectangular surface geometries (e.g., channel sizes).

can accumulate in living bacterial cells and is lost when a cell is damaged, thus a decrease or loss of the reporter stain in the presence of an antibiotic is indicative of antibiotic-induced cell death. It is preferred that the levels of a reporter stain can be measured in real time to provide rapid detection of antibiotic susceptibility to an antibiotic. The reporter stain can be e.g., a fluorescent dye, a colorimetric agent, a luminescent agent, a chemiluminescent agent, a fluorophore, a pH sensi- Shear Rate/Shear Stress (SR)
Formula for shear rate $(6 * Q)/(w * h^2)$

| w [μm] 250 h [μm] 125 | | w [μm] 300 h [μm] 150 | | w [μm] 350 h [μm] 175 | | w [μm] 400 h [μm] 200 | | w [μm] 400 h [μm] 205 | |
|---|---|---|---|---|---|---|---|---|---|
| Q [ml/h] | SR [1/s] | Q [ml/h] | SR [1/s] | Q [ml/h] | SR [1/s] | Q [ml/h] | SR [1/s] | Q [ml/h] | SR [1/s] |
| 20 | 8533.333333 | 20 | 4938.271605 | 20 | 3109.815355 | 20 | 2083.333333 | 20 | 1982.946659 |
| 40 | 17066.66667 | 40 | 9876.54321 | 40 | 6219.630709 | 40 | 4166.666667 | 40 | 3965.893317 |
| 60 | 25600 | 60 | 14814.81481 | 60 | 9329.446064 | 60 | 6250 | 60 | 5948.839976 |
| 80 | 34133.33333 | 80 | 19753.08642 | 80 | 12439.26142 | 80 | 8333.333333 | 80 | 7931.786635 |
| 100 | 42666.66667 | 100 | 24691.35802 | 100 | 15549.07677 | 100 | 10416.66667 | 100 | 9914.733294 |
| 120 | 51200 | 120 | 29629.62963 | 120 | 18658.89213 | 120 | 12500 | 120 | 11897.67995 |
| 140 | 59733.33333 | 140 | 34567.90123 | 140 | 21768.70748 | 140 | 14583.33333 | 140 | 13880.62661 |
| 160 | 68266.66667 | 160 | 39506.17284 | 160 | 24878.52284 | 160 | 16666.66667 | 160 | 15863.57327 |
| 180 | 76800 | 180 | 44444.44444 | 180 | 27988.33819 | 180 | 18750 | 180 | 17846.51993 |
| 200 | 85333.33333 | 200 | 49382.71605 | 200 | 31098.15355 | 200 | 20833.33333 | 200 | 19829.46659 |
| 220 | 93866.66667 | 220 | 54320.98765 | 220 | 34207.9689 | 220 | 22916.66667 | 220 | 21812.41325 |
| 240 | 102400 | 240 | 59259.25926 | 240 | 37317.78426 | 240 | 25000 | 240 | 23795.3599 |
| 260 | 110933.3333 | 260 | 64197.53086 | 260 | 40427.59961 | 260 | 27083.33333 | 260 | 25778.30656 |
| 280 | 119466.6667 | 280 | 69135.80247 | 280 | 43537.41497 | 280 | 29166.66667 | 280 | 27761.25322 |
| 300 | 128000 | 300 | 74074.07407 | 300 | 46647.23032 | 300 | 31250 | 300 | 29744.19988 |
| 320 | 136533.3333 | 320 | 79012.34568 | 320 | 49757.04568 | 320 | 33333.33333 | 320 | 31727.14654 |
| 340 | 145066.6667 | 340 | 83950.61728 | 340 | 52866.86103 | 340 | 35416.66667 | 340 | 33710.0932 |
| 360 | 153600 | 360 | 88888.88889 | 360 | 55976.67638 | 360 | 37500 | 360 | 35693.03986 |
| 380 | 162133.3333 | 380 | 93827.16049 | 380 | 59086.49174 | 380 | 39583.33333 | 380 | 37675.98652 |
| 400 | 170666.6667 | 400 | 98765.4321 | 400 | 62196.30709 | 400 | 41666.66667 | 400 | 39658.93317 |
| 420 | 179200 | 420 | 103703.7037 | 420 | 65306.12245 | 420 | 43750 | 420 | 41641.87983 |
| 440 | 187733.3333 | 440 | 108641.9753 | 440 | 68415.9378 | 440 | 45833.33333 | 440 | 43624.82649 |
| 460 | 196266.6667 | 460 | 113580.2469 | 460 | 71525.75316 | 460 | 47916.66667 | 460 | 45607.77315 |
| 480 | 204800 | 480 | 118518.5185 | 480 | 74635.56851 | 480 | 50000 | 480 | 47590.71981 |
| 500 | 213333.3333 | 500 | 123456.7901 | 500 | 77745.38387 | 500 | 52083.33333 | 500 | 49573.66647 |
| 40 | 17066.66667 | 40 | 9876.54321 | 40 | 6219.630709 | 40 | 4166.666667 | 40 | 3965.893317 |
| 60 | 25600 | 60 | 14814.81481 | 60 | 9329.446064 | 60 | 6250 | 60 | 5948.839976 |
| 80 | 34133.33333 | 80 | 19753.08642 | 80 | 12439.26142 | 80 | 8333.333333 | 80 | 7931.786635 |
| 100 | 42666.66667 | 100 | 24691.35802 | 100 | 15549.07677 | 100 | 10416.66667 | 100 | 9914.733294 |

Flow Media for Generating Shear Stress

It is contemplated herein that the liquid medium used to generate a flow velocity across an immobilized bacterium is, at the least, a minimal media capable of sustaining bacterial cells and permitting repair of damage caused by the mechanical stress. It is well within the abilities of one skilled in the art to choose a medium that sustains bacterial cell repair. Any standard bacterial medium, such as Mueller Hinton broth, can be used as a flow medium. The temperature, and concentration of the medium can also be varied to optimize conditions that are useful for a variety of different bacterial strains.

The flow medium also comprises a reporter stain, which is an agent comprising a detectable moiety that is added to the medium to permit visualization of cell damage and/or cell death. A reporter stain can be any stain that (i) accumulates preferentially in damaged or dying bacterial cells compared to undamaged or repaired cells or (ii) is excluded preferentially in damaged or dying cells compared to undamaged or repaired cells and that provides a detectable signal. For example, a reporter stain can be a fluorescent dye that stains only damaged or dying bacterial cells and an increase in fluorescence in the presence of an antibiotic is indicative of antibiotic-induced cell death. Alternatively, a reporter stain tive dye, a depolarization sensitive dye, among others. In one embodiment, the reporter stain emits within the visible range (e.g., having a wavelength of approximately 390-750 nm). It is also contemplated herein, in one embodiment that a plurality (e.g., at least two) of different reporter stains are used together, for example, with one agent staining dead or dying cells and the other agent staining living or repaired cells. In this embodiment, the ratio of the two reporter stains can be used as a quantitative or qualitative measure of dead cells (e.g., antibiotic sensitive cells) to repaired cells (e.g., antibiotic resistant cells).

In one embodiment, the reporter stain used with the methods and devices described herein is a fluorescent dye. A fluorescent dye can be added to the medium for visualizing cellular damage. The fluorescent stains can be chosen such that they do not enter the cells unless the cell wall is permeabilized or the membrane potential changes, and thus will not interfere with cellular repair. In one embodiment, a fluorescent dye/stain useful with the methods and devices described herein meets the following criteria: (1) effectively stains both gram-negative and gram-positive bacteria, (2) does not damage cells and is not toxic to cells, (3) can be used directly in a growth medium, and (4) does not require pre-treatment processing steps (e.g., fixation or centrifugation). Two non-limiting and exemplary candidate dyes that meet the above criteria are Sytox Green and DiBAC$_4$(3). Sytox green stains nucleic acids and is an unsymmetrical cyanine dye with three positive charges. DiBAC$_4$(3) is a membrane-potential sensitive dye.

Chemical Stress

Damage to the bacterial cell can also be induced through chemical stress. This is particularly important in some cases where the mechanical shear forces generated by the apparatus described herein are insufficient to damage the bacteria in such a way that the cells are forced to activate their biochemical pathways to repair the cell wall. Chemical stress can be used alone to induce damage to the cell, or alternatively can be used in combination with mechanical stress. Some non-limiting examples of chemical stressors include, e.g., acidic pH (pH 2-7), basic pH (pH 7-10), oxidative stress (e.g., exposure to hydrogen peroxide), enzymatic stress (e.g., lysostaphin, endolysins, lysozyme), osmotic stress (e.g., high or low ionic salt to add osmotic pressure to the cells) or porins (e.g., gramicidin). One of skill in the art can easily optimize the amount and type of chemical stressor that permits non-lethal damage to the immobilized bacteria, yet substantially restricts entry of a reporter agent that stains dead or dying cells (e.g., fluorescent dye) in the absence of an antibiotic.

In one embodiment, the agent that causes chemical stress to bacteria is lysostaphin, which is a glycylglycine endopeptidase that specifically cleaves the pentaglycine cross bridges found in the staphylococcal peptidoglycan. At high enough concentrations, lysostaphin kills *S. aureus* within minutes ([MIC$_{90}$] 0.001 to 0.064 µg/mL) (Wu, J. A., et al., *Antimicrob Agents Chemother* (2003) 47(11):3407-14). One of skill in the art can easily tailor the dose of lysostaphin necessary to chemically damage the cell wall to a level appropriate for use with the methods and devices described herein (e.g., non-lethal, repairable damage). Lysostaphin may be introduced transiently or continually to effect the changes required.

An alternate chemical damage mechanism is to introduce low levels of bacteriophage endolysins, which specifically damage the cell walls of Staphylococci (Donovan, D. M., et al., *FEMS Microbiol Lett* (2006) 265(1):133-9; O'Flaherty, S., et al., *J Bacteriol* (2005) 187(20):7161-4). The endolysin strategy is likely to be more broadly applicable across Staphylococci strains as compared to lysostaphin, since they have multiple putative antimicrobial activities (e.g., the phi11 endolysin is a peptidoglycan hydrolase that exhibits both endopeptidase and amidase activities) (Donovan, D. M., et al., *FEMS Microbiol Lett* (2006) 265(1):133-9). The endolysins, when purified and exposed to bacteria externally, can cause exolysis ("lysis from without"). One of skill in the art can prepare a purified endolysin by e.g., amplifying an endolysin gene by PCR, cloning it into e.g., a pET vector (Novagen), over-expressing the gene in *E. coli*, and purifying the endolysins using a nickel column (Donovan, D. M., et al., *FEMS Microbiol Lett* (2006) 265(1):133-9; Sass, P. and G. Bierbaum *Appl Environ Microbiol* (2007) 73(1):347-52).

Antibiotics

Essentially any antibiotic can be used with the methods and devices described herein. Particularly relevant antibiotics include those that are used in the clinic, however it is also contemplated herein that a candidate antibiotic can also be tested for efficacy in this manner. Examples of the different classes of antibiotics useful with the methods and devices described herein include, but are not limited to, beta lactam antibiotics, beta lactamase inhibitors, aminoglycosides and aminocyclitols, quinolones, tetracyclines, macrolides, and lincosamides, as well as glycopeptides, lipopeptides and polypeptides, sulfonamides and trimethoprim, chloramphenicol, isoniazid, nitroimidazoles, rifampicins, nitrofurans, methenamine, and mupirocin, all of which can be used in conjunction with the methods described herein.

In one embodiment, the antibiotic is a cell wall biosynthesis inhibitor. An exemplary family of antibiotics that inhibit cell wall biosynthesis include the beta lactam antibiotics (e.g., penicillin derivatives, cephalosporins, monobactams, carbapenems, and β-lactamase inhibitors). Some non-limiting examples of cell wall biosynthesis inhibitors include penicillin, ampicillin, benzathine penicillin, benzylpenicillin (penicillin G), phenoxymethylpenicillin (penicillin V), procaine penicillin, oxacillin, methicillin, nafcillin, cloxacillin, dicloxacillin, flucloxacillin, temocillin, amoxycillin, co-amoxiclav (amoxicillin+clavulanic acid), azlocillin, carbenicillin, ticarcillin, mezlocillin, piperacillin, aztreonam, bacitracin, cephalosporin, cephalexin, cefadroxil, cefalexin, cefprozil, cefdinir, cefdiel, cefditoren, cefoperazone, cefobid, cefotaxime, cefpodoxime, ceftazidime, ceftibuten, ceftizoxime, ceftriaxone, cefepime, ceftobiprole, cephalothin, cefazolin, cefaclor, cefuroxime, cefamandole, cefotetan, cefoxitin, ceftriaxone, cefotaxime, cefpodoxime, ceftazidime, carbapenem, imipenem (with cilastatin), meropenem, ertapenem, faropenem, doripenem, aztreonam, clavulanic acid, tazobactam, sulbactam, vancomycin, teicoplanin, loracarbef, and ramoplanin.

Antibiotic—Mechanism of Action

In one embodiment, it is preferred that the antibiotic used has a mechanism of action that inhibits cell wall synthesis. These antibiotics are preferred because repair of the cell wall in the presence of a cell wall synthesis inhibitor is a direct measure of antibiotic resistance, since the mechanism of antibiotic action inhibits repair necessitated the stressor-induced damage. The methods and devices described herein produce cellular damage to the cell wall of a bacterium, permitting fluorescent dye to be taken up by damaged cells. The damaged cells activate metabolic synthesis of the cell wall in order to repair the stressor-induced damage. Therefore, susceptibility to an antibiotic that prevents the re-synthesis of the cell wall (such as those described above) can be readily monitored by e.g., assessing the intensity of fluorescence of a dye taken up by the damaged cells or extruded by cells undergoing repair.

It is also contemplated herein that antibiotics having another mechanism of action can be tested using the methods described herein, even if the effect on cell wall repair is indirect. Often changes in cellular processes are reflected by the state of the cell wall, which permits one to use the methods described herein even if the antibiotic is not a cell wall synthesis inhibitor. It is well within the abilities of one of skill in the art to adapt the methods described herein for cell wall synthesis inhibitors, such that the methods can be used with antibiotics having another mechanism of action. For example, antibiotics that inhibit protein synthesis can be tested by inducing damage to the cell (e.g., by physical or chemical stress) that necessitates protein synthesis of e.g., peptidoglycan to repair the cell wall. A cell that is able to continue protein synthesis in the presence of the antibiotic and thus repair the cell wall is determined to be resistant to the antibiotic, while cells that cannot repair the cell wall are considered to be susceptible to the antibiotic.

It is also contemplated herein that a physical stress as described herein can also damage other cellular functions, whose repair can be monitored in the presence of an antibiotic that targets that function.

Antibiotics with a different mechanism of action (e.g., DNA synthesis inhibitors, protein synthesis inhibitors etc) are also contemplated for use and the methods described herein for cell wall synthesis inhibitors can be generalized for use with these antibiotics. In general, the stressor-induced damage is matched with the mechanism of action of the antibiotic; that is the stressor will induce a metabolic repair pathway to be turned on, permitting one to measure the recovery of the cell in the presence of an antibiotic that aims to inhibit the induced metabolic pathway. For example, to test susceptibility to an antibiotic that inhibits DNA synthesis, one would induce DNA damage by e.g., UV radiation thus activating the cell to repair DNA and then monitor DNA synthesis rates by e.g., labeled-thymidine incorporation in the presence of a DNA synthesis inhibitor. If there is a decrease in the level of thymidine incorporation (e.g., the cell is unable to repair itself) in the presence of an antibiotic, the cell is susceptible to the antibiotic. Alternatively, if there is no change in the level of thymidine incorporation among cells in the presence and absence of the antibiotic (e.g., the cell is capable of repair), the cell is determined to be resistant to the antibiotic.

Screening Candidate Antibiotics

The methods and devices described herein can be used to screen candidate antibiotics for efficacy against a bacterial sample, a bacterial strain or a mix of bacterial strains. In one embodiment, the device described herein comprises a plurality of channels to which bacterial cells are immobilized. In such a multi-channel system, one can screen a plurality of candidate antibiotics (e.g., one antibiotic per channel) or screen one antibiotic against a plurality of bacterial strains (e.g., one bacterial strain per channel). One can also use the methods and devices described herein to test a range of doses for an antibiotic or candidate antibiotic, determine efficacy of an antibiotic, and/or to determine a minimum inhibitory concentration for an antibiotic or candidate antibiotic.

Determining Minimum Inhibitory Concentration (MIC)

As used herein, the term "minimum inhibitory concentration" refers to the lowest concentration of an antibiotic that will inhibit the visible growth of a microorganism. In the context of the present invention, the term "minimum inhibitory concentration" also encompasses the lowest concentration of an antibiotic that effects cell death or inhibits cell wall repair using the methods and devices described herein. In one embodiment, the methods and devices described herein permit the determination of a minimum inhibitory concentration for an antibiotic or candidate antibiotic against a bacterial strain. In one embodiment, the minimum inhibitory concentration of an antibiotic can be determined by measuring a modulation in the response of the bacterial cells (e.g., uptake or extrusion of a reporter stain, change in morphology, change in metabolism, etc) in a channel exposed to an antibiotic compared to the same bacterial cells in a channel not exposed to the antibiotic or to different concentrations of the same antibiotic.

The minimum inhibitory concentration is a clinically relevant value indicating the minimum effective dose of an antibiotic to be administered to a subject to induce bacterial cell death and/or reduce at least one symptom of the bacterial-mediated disease. Clinically, the minimum inhibitory concentrations are used not only to determine the amount of antibiotic that a subject will receive but also to determine the preferred antibiotic to be used. A minimum inhibitory concentration can also be determined for a candidate antibiotic to permit e.g., efficacy determination and dosing information for clinical trials.

One can easily test a range of antibiotic concentrations using e.g., the 4-channel device described herein in the Example section or another device comprising a plurality of channels as described herein to determine a dose response relationship for the antibiotic.

Devices

Figure 5:
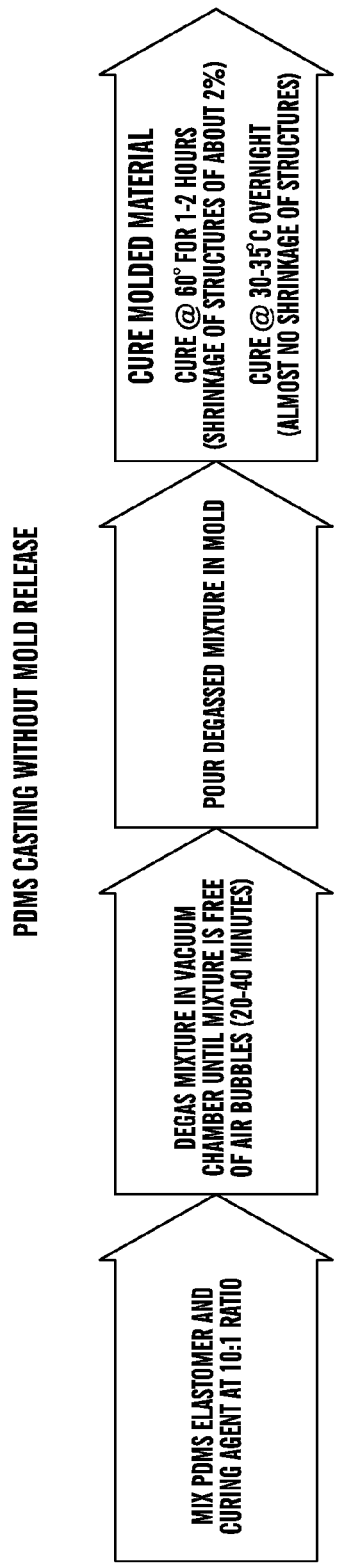
FIG. 5 shows an exemplary process to create a flow cell by casting a molded rubber chip using poly-dimethylsiloxane (PDMS).
Figure 6:
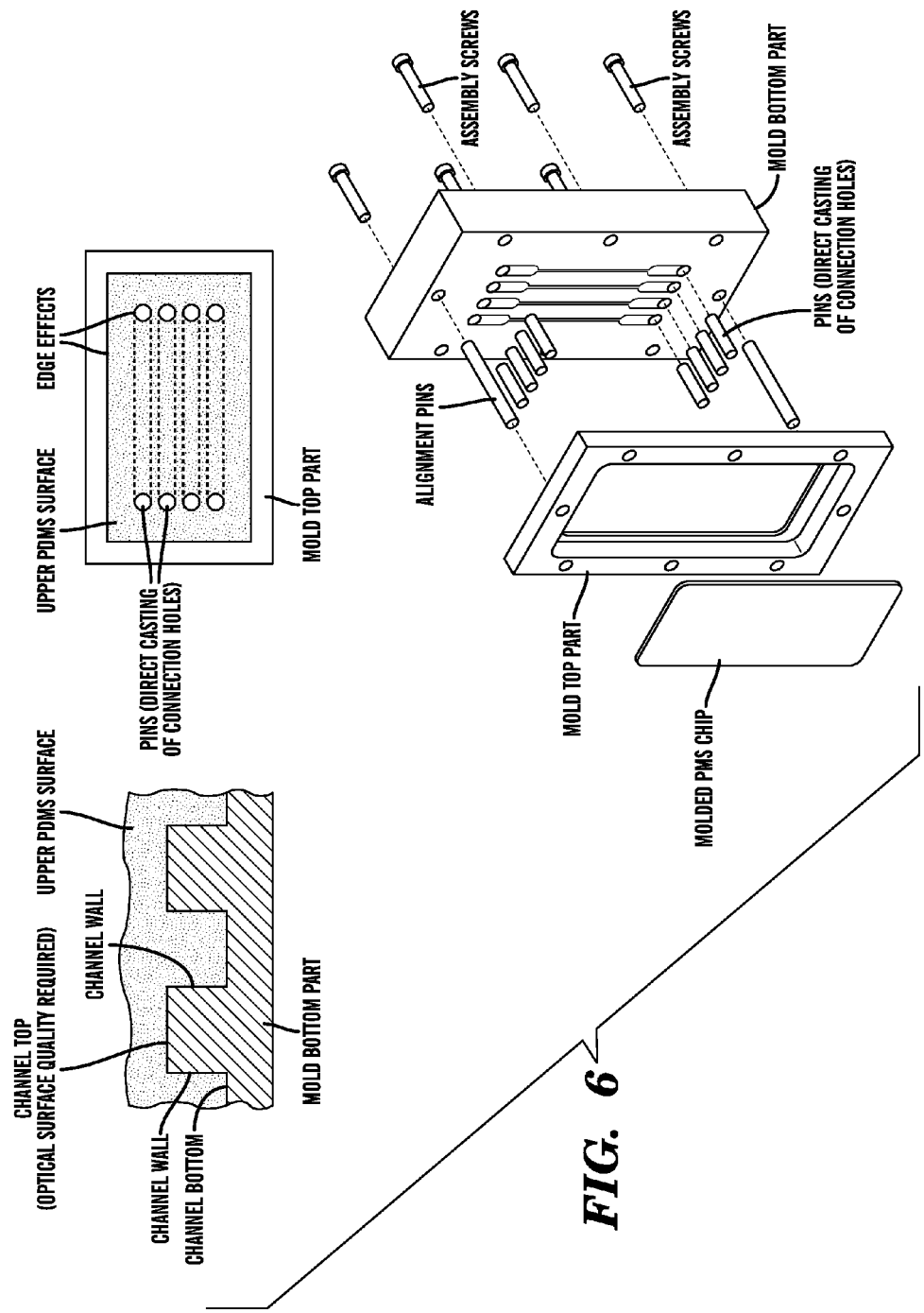
FIG. 6 shows an exemplary mold design for casting a molded rubber chip using poly-dimethylsiloxane (PDMS). Casting mold consists of (1) mold bottom part (channels); (2) mold top part (walls); and pins (holes). Aluminum a mold material allows faster manufacturing, diamond turning without surface treatment, but filigree structures are easily damaged if not handled properly. The flatness of upper PDMS surface is specified by viscosity, surface tension, and edge effects. Basic geometry manufactured by milling: (1) inner corners need to have radii; (2) space between the channels need to be big enough for allowing the end mill to pass through; (3) required parallelism of channel top and bottom surface require planning of stock material; and (4) due to planning the surface quality if defined by the planning process.
Figure 7:
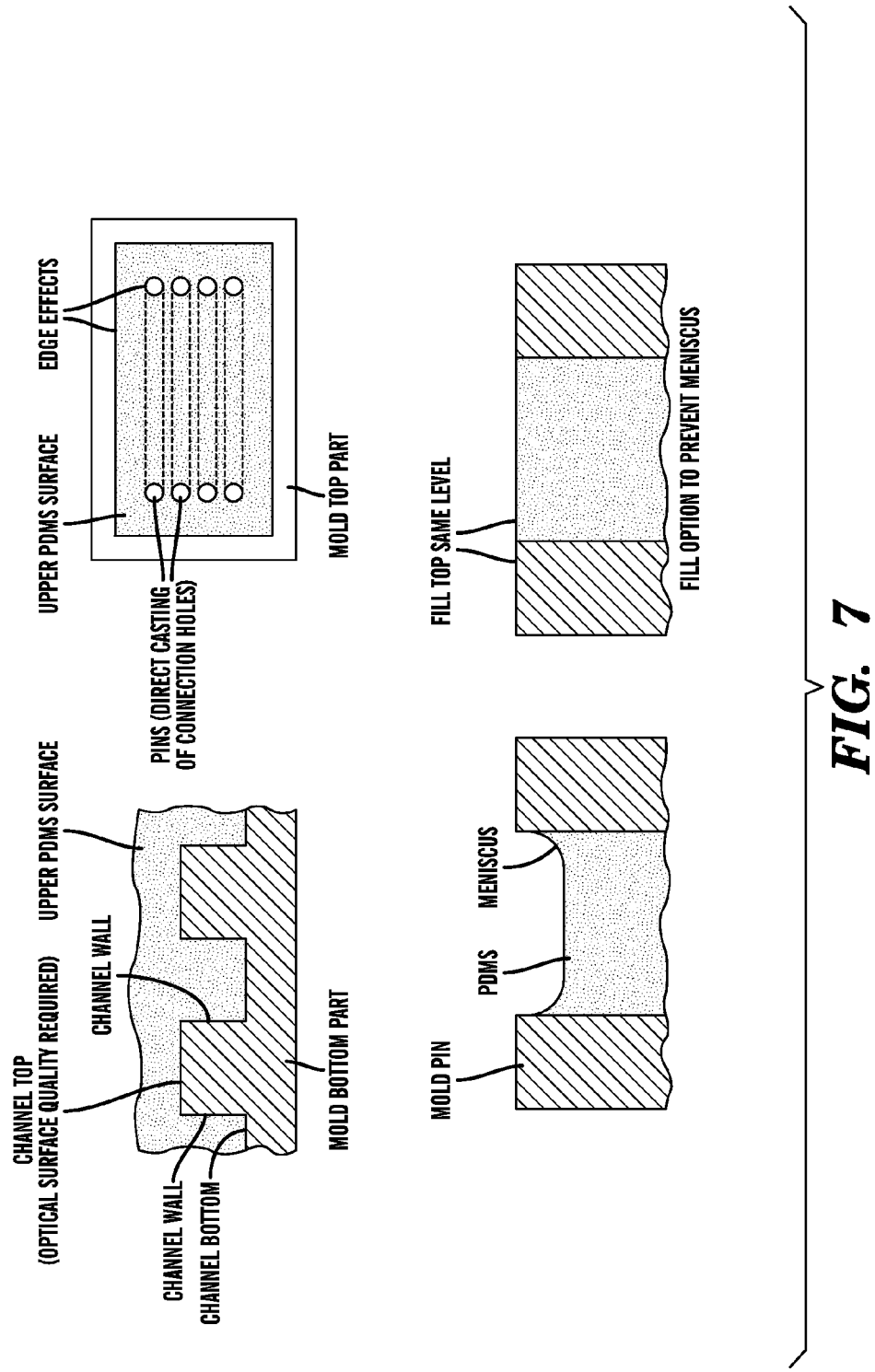
FIG. 7 shows an exemplary method for casting a molded rubber chip using poly-dimethylsiloxane (PDMS) and considerations with regard to PDMS casting effects. Surface qualities are defined by milling process: (1) channel top; (2) channel bottom; and (3) channel wall. Surface qualities are defined by fluid effects: upper PDMS surface. Critical surface qualities: channel top (optional). Critical dimensional tolerances: (1) height of the channel (±5 µm); (2) parallelism of channel top and channel bottom (±5 µm); and (3) width of channel (±5 µm). Edge effects: (1) capillary effect causes meniscus at mold-PDMS intersection; (2) effect occurs at pins and mold top part edge; (3) effect at mold top part has negative effects for sealing (preventing by filling the PDMS to the same height as the mold); (4) effect at the pins can be useful for sealing (meniscus is used like an O-ring).

In some embodiments, a device as described herein is contemplated to have a plurality of channels (e.g., at least 2, 3, 4, 5, 6, 7, 8, 9, 10, 12, 15, 20, 24, 25, 30, 36, 40, 48, 50, 55, 60, 70, 80, 90, 100, or more) with each channel corresponding to a different antibiotic and/or a different bacterial sample. In addition, each channel can correspond to a different dose or concentration of a particular antibiotic tested against an immobilized bacterial strain. In one embodiment, the plurality of channels are arranged in parallel. The channels can be formed using e.g., silicone or silicone rubber as described, for example, herein in the Examples section (FIGS. 5, 6, and 7). In one embodiment, the channels are disposable, but it is also contemplated herein that the channels are re-used with the methods and devices used herein. The device described herein is designed for use with a solid support to which a bacterium is immobilized. It is preferred that the solid support is disposable to prevent cross-contamination between bacterial samples. The solid supports are entirely removable from the device but are used with the assay system described e.g., in the methods described herein. In one embodiment, the device comprises a microscope with an optical stage that can be controlled in the X, Y and Z planes.

In one embodiment, a sample derived from a patient can be tested concurrently with multiple antibiotics in a plurality of channels. While it can be manually detected (e.g., using a microscope), in one embodiment the device detects e.g., fluorescence emission and the intensity of a signal using an agent as described herein and displays the location (e.g., channel) matching the antibiotic for the user. If several antibiotics produce a detectable signal, the antibiotic with the highest intensity of signal is then administered to the patient by a skilled clinician.

In some embodiments, the device further comprises immobilized bacteria. Such a device is particularly useful for screening candidate antibiotic molecules. It is contemplated herein that such a device comprises a plurality of channels to permit high-throughput screening of a e.g., small molecule library. The device comprises a detector that detects fluorescence intensity concurrently from the plurality of channels. Fluorescence data from the detector is then stored and/or the computer determines the location of a fluorescence signal on e.g., a chip comprising the plurality of channels. The computer then displays the location of any molecules that have antibiotic efficacy.

In one embodiment, the device described herein comprises at least one pump to control the flow velocity or flow rate of a medium through a channel lined with bacterial cells. In one embodiment, a single pump is used to achieve a flow velocity consistent across a plurality of channels. This has the added advantage of maintaining substantially similar assay conditions for the antibiotic testing channel(s) compared to one or more control channels that lack antibiotic, and permitting the detected levels of the reporter stain in the testing channel(s) to be normalized to background levels in the control channel(s). In one embodiment, the flow velocity in each channel of a plurality of channels in the device can be controlled by a plurality of pumps (e.g., 1 pump per channel, 1 pump/2 channels, 1 pump/5 channels, 1 pump/10 channels).

In one embodiment of the methods and devices described herein, the method is completely automated. The device can be automated (e.g., using software) such that the total fluorescence in a location of each channel is scanned, measured and/or delivered to a computer or other data storage device. Each channel can be scanned for e.g., fluorescence simultaneously with other channels or in a sequential manner where one channel is scanned after another. The channels are scanned iteratively during the assay process, however the location within the channel (e.g., optical view) for each iterative measurement will be substantially identical to prevent artifactual measurements of reporter stain intensity. The timing (e.g., cycle) between each iterative measurement can be chosen by one of skill in the art. For example, the intensity of the reporter stain (e.g., fluorescence) in a channel can be measured every 30 sec, every minute, every 2 min, every 3 min, every 4 min, every 5 min, every 10 min, every 15 min, every 20 min, every 30 minutes or more over a length of time desired by one of skill in the art. In another embodiment, the device described herein comprises a handheld device that is entirely portable. While not necessary for the methods described herein, in one embodiment the device further comprises a microscope. Alternatively, in another embodiment, the device does not comprise a microscope.

Systems

Embodiments of the invention also provide for systems (and computer readable media for causing computer systems) to perform a method for determining whether a bacterium is susceptible to an antibiotic by measuring e.g., fluorescence emission.

Embodiments of the invention have been described through functional modules, which are defined by computer executable instructions recorded on computer readable media and which cause a computer to perform method steps when executed. The modules have been segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs, that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable medium described herein, may be distributed across one or more of such components, and may be in transition there between.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system, a storage device, a comparison module and a display module. The functional modules can be executed on one, or multiple, computers, or by using one, or multiple, computer networks. The determination system has computer executable instructions to provide e.g., fluorescence information in computer readable form.

The determination system, #40, can comprise any system for detecting a signal from an agent comprising a reporter moiety. Such systems can include, flow cytometry systems, fluorescence assisted cell sorting systems, fluorescence microscopy systems (e.g., fluorescence microscopy, confocal microscopy), and other systems for measuring fluorescence emission. It is contemplated herein that a detector from a microfluidics system can be used as the determination system.

The information determined in the determination system can be read by the storage device #30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon sequence information or expression level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising the sequence information or expression level information.

In one embodiment the reference data stored in the storage device to be read by the comparison module is fluorescence emission data obtained from a stressed bacterium in the absence of antibiotic.

The "comparison module" #80, 90 can use a variety of available software programs and formats for the comparison operative to compare fluorescence data determined in the determination system to reference samples and/or stored reference data. In one embodiment, the comparison module is configured to use pattern recognition techniques to compare sequence information from one or more entries to one or more reference data patterns. The comparison module may be configured using existing commercially-available or freely-available software for comparing patterns, and may be optimized for particular data comparisons that are conducted. The comparison module provides computer readable information related to the antibiotic susceptibility that can include, for example, detection of fluorescence, fluorescence intensity etc.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, #100, may be a fluorescence intensity profile showing comparative sensitivity among a panel of antibiotics #140. In one embodiment, the content based on the comparison result is a signal indicative of the susceptibility of a bacterium to a particular antibiotic #140.

In one embodiment of the invention, the content based on the comparison result is displayed on a computer monitor #120. In one embodiment of the invention, the content based on the comparison result is displayed through printable media #130. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The present invention therefore provides for systems (and computer readable media for causing computer systems) to perform methods for determining whether a bacterium is susceptible to a particular antibiotic.

Systems and computer readable media described herein are merely illustrative embodiments of the invention for performing methods of determining whether a bacterium is susceptible to an antibiotic, and is not intended to limit the scope of the invention. Variations of the systems and computer readable media described herein are possible and are intended to fall within the scope of the invention.

The modules of the machine, or used in the computer readable medium, may assume numerous configurations. For example, function may be provided on a single machine or distributed over multiple machines.

Advantages of the Methods Described Herein

The current methodologies for measuring antimicrobial susceptibility include dilution testing, disk diffusion, Etest, latex agglutination, specialized CHROMagars, mechanized or semi-automated systems based on dilution testing, and PCR. These current standard methods for detecting antibiotic susceptibility are based on the ability of the bacteria to proliferate in the presence of antibiotics, and thus these techniques are time-consuming, costly, and insensitive, particularly for evaluation of slow-growing organisms. To develop a truly rapid susceptibility test, one must circumvent the need for growth.

Described herein is a novel method for rapid antibiotic susceptibility detection in e.g., less than an hour. The methods and devices described herein have the potential to revolutionize clinical practice for bacterial infections by enabling clinicians to prescribe appropriate antibiotic therapy much sooner than is possible with current methods. The methods and devices can also be multiplexed (multiple antibiotics and/or multiple organisms) and can be integrated with current bacterial identification methodologies.

The methods and devices described herein can also be used to complement existing rapid tests based on molecular diagnostics (e.g. PCR) because they would provide a low-cost rapid method that delivers clinically actionable information (susceptibility profiles). While genetic tests provide precise information for epidemiological studies, the high reagent costs, relatively high operator skills required, and limited clinical utility continue to limit widespread routine use. Furthermore, the molecular diagnostics suffer from a high number of false positives and unacceptable performance in non-sterile specimens due to the co-presence of methicillin-sensitive *S. aureus* and methicillin-resistant coagulase-negative staphylococci (von Eiff, C., et al., *J Antimicrob Chemother* (2008) 61(6):1277-80; E Becker, K., et al., *J Clin*

*Microbiol* (2006) 44(1):229-31). This limitation has been overcome in some assays by linking detection of the mecA gene with detection of a neighboring orfX gene, however flanking regions can be heterogeneous and lead to false negatives (Huletsky, A., et al., *J Clin Microbiol* (2004) 42(5): 1875-84). Since the methods described herein can be automated and are based on phenotypic changes, the methods are useful for routine clinical diagnostic and providing clinicians with the information they need to treat their patients, namely what antibiotic to use and at what dosage.

Rapid methods, such as the methods described herein, has the following advantages as compared to traditional methods: (1) informs physicians and influences their treatment decisions sooner (Matsen, J. M., *Diagn Microbiol Infect Dis* (1985) 3(6 Suppl):73S-78S; Vincent, P., *Presse Med* (1985) 14(32):1697-700), (2) reduces mortality rates (Doern, G. V., et al., *J Clin Microbiol* (1994) 32(7):1757-62), (3) significantly reduces the number of laboratory studies, imaging procedures, days of intubation, and days spent in the intensive care unit (Doern, G. V., et al., *J Clin Microbiol* (1994) 32(7): 1757-62), and (4) reduces the overall costs of hospitalization (Doern, G. V., et al., *J Clin Microbiol* (1994) 32(7):1757-62; Barenfanger, J., et al., *J Clin Microbiol* (1999) 37(5):1415-8). Moreover, as bacterial populations become more resistant to available antibiotics, it becomes more critical that physicians move to targeted narrow-spectrum antibiotic therapy. This can only be accomplished with the assistance of new antibiotic susceptibility methodologies such as the methods described herein that provide results in a fraction of the time of current protocols.

Traditional Tests for Antibiotic Susceptibility

The traditional tests for antibiotic susceptibility and the limitations of these tests are described herein below.

Traditionally, antibiotic susceptibility was determined either by a dilution or disk diffusion technique (Henry, J. B., ed. Clinical Diagnosis and Management by Laboratory Methods. 20th ed. 2001, Saunders: Philadelphia). In the dilution test, the microorganism is inoculated into a series of tubes or wells containing a range of concentrations of the antibiotic. The lowest inhibitory antibiotic concentration is termed the minimum inhibitory concentration (MIC). In the disk diffusion test, a paper disk containing a specified amount of antibiotic is applied to an agar surface that has been freshly inoculated with a lawn of microorganisms. The antimicrobial diffuses from the disk, resulting in a zone of inhibition at which a critical concentration of the antibiotic in the medium inhibits growth at a particular point in time (typically 18-24 hrs after inoculation). The zone diameter is measured and compared to standards to define susceptibility and resistance. The zone diameter is inversely related to the MIC, i.e. the larger zones indicate lower MICs.

The Etest is based on the diffusion of a continuous concentration gradient of an antibiotic from a plastic strip into an agar medium. The plastic strip has a predefined concentration of dried drug on one side and a MIC scale on the other which allows a read out of the zone of inhibition and corresponding MIC after incubating the Etest strip a freshly inoculated microbial lawn under the appropriate conditions. Although the Etest's ease of use makes it a preferred option over traditional diffusion or dilution testing, the cost is prohibitive for most laboratories to use on a routine basis for primary screening.

Specifically for identifying methicillin resistance in *Staphylococcus aureus* strains, Oxoid offers a rapid latex agglutination test for PBP2a wherein latex particles sensitized with a monoclonal antibody against PBP2a will react with MRSA to cause macroscopic agglutination. The kit includes two extraction reagents, and the agglutination reaction is performed on heated extracts of bacterial colonies. MRSA colonies can be detected within 15 min; however latex agglutination kits tend to be less sensitive than other susceptibility methods. For example, when comparing this kit to the oxacillin screen agar method using isolated colonies from blood cultures positive for *S. aureus* (n=70), the direct PBP2a test was only 18% sensitive.

According to the results from proficiency testing programs of the College of American Pathologists, most labs in the U.S. now use microdilution based semi-automated systems (Henry, J. B., ed. Clinical Diagnosis and Management by Laboratory Methods. 20th ed. 2001, Saunders: Philadelphia). The shift away from the more traditional methods is a response to the efficiency gains from replicate inoculations of combined identification and susceptibility systems and the need for data management systems. Two popular systems are the VITEK (BioMerieux) and Microscan WalkAway (Dade Behring). In the VITEK system, antimicrobials are contained in miniature wells on a plastic card. The cards are incubated in the associated reader/incubator instrument, and the wells are monitored via optical density. Although bacterial identification can be obtained within 4 hours, the mean time of incubation for antimicrobial susceptibility testing is approximately 8 hours (Eigner, U., et al., *J Clin Microbiol* (2005) 43(8): p. 3829-34). The Microscan Walkaway conducts endpoint photometric measurements, for which bacterial identification is available approximately within 3-5 hours, but antibacterial susceptibility results are available no sooner than 9 hours (Henry, J. B., ed. Clinical Diagnosis and Management by Laboratory Methods. 20th ed. 2001, Saunders: Philadelphia; Sellenriek, P., et al (2005) 105*th General Meeting of the American Society for Microbiology* Atlanta, Ga.). However a recent evaluation of the Microscan for susceptibility testing of gram positive organisms found it took an average of 23.3 hours before susceptibility results were available (McCarter, Y. S., et al., 105*th General Meeting of the American Society for Microbiology* (2005) Atlanta, Ga.). One advantage of the Microscan is that the results are also interpretable by eye if there is a problem with the instrument, which is an appealing feature to lab directors.

In recent years, several targeted methods have emerged in the marketplace to address the need for rapid detection of specific pathogens. In the case of MRSA, two noteworthy offerings are available from Becton Dickenson; CHROMagar MRSA and GeneOhm StaphSR assay. The CHROMagar MRSA is a selective and differential medium for the qualitative direct detection of nasal colonization by methicillin resistant *S. aureus* (MRSA) to aid in the prevention and control of MRSA infections in healthcare settings. The test is performed on anterior nares swabs to screen for MRSA colonization but is not intended to diagnose MRSA infection or provide information to guide treatment, such as MIC or susceptibility profiles. The results from a CHROMagar plate are available within 24-48 hrs, but occasional strains of coagulase-negative staphylococci or corynebacteria may grow on CHROMagar. Thus, a confirmatory coagulase test is necessary for MRSA confirmation. The GeneOhm StaphSR assay is a PCR based assay that rapidly provides simultaneous identification of methicillin-susceptible *S. aureus* (MSSA) and methicillin-resistant *Staphylococcus aureus* (MRSA) and was recently cleared by the FDA for the direct detection of MRSA from patients with positive blood cultures and for individuals positive for MRSA nasal colonization. The GeneOhm assay provides targeted information (SA identification and mecA detection) within a few hours, but again does not provide phenotypic information (MIC or susceptibility profiles).

These methods are useful for screening, but do not provide the critical information that a physician needs for treatment, namely which antibiotic to prescribe to the patient. Furthermore, although the techniques are rapid, they are also significantly more expensive than the more traditional methods. The combination of incomplete information and increased cost limit the usefulness of these tests in routine use.

The more traditional methods, such as dilution, disk diffusion, or Etest techniques, are accurate and inexpensive, but are lengthy and require significant operator time. The accuracy of these methods depends on strict adherence to standard methods, including the medium used, inoculation size, and incubation conditions (Henry, J. B., ed. Clinical Diagnosis and Management by Laboratory Methods. 20th ed. 2001, Saunders: Philadelphia). The automated susceptibility systems provide decreases in turn-around time and operator time, but can add significant cost to the tests. Moreover these semi-automated systems do not provide information in time to influence initial treatment decisions. PCR and CHROMagars can be useful in outbreaks, but are not appropriate for broad spectrum diagnosis due to limited information and high cost.

Flow Cytometry Methods

As early as 1982, researchers began studying changes in bacteria incubated with various active agents via flow cytometry (Steen, H. B., et al., Cytometry (1982) 2(4):249-57). The early studies focused on morphology, cell cycle kinetics, DNA replication, and bacterial metabolism (Steen, H. B., et al., supra; Boye, E. and A. Lobner-Olesen Res Microbiol (1991) 142(2-3):131-5; Fouchet, P., et al., Biol Cell (1993) 78(1-2): 95-109; Martinez, O. V., et al., Cytometry (1982) 3(2):129-33). The general format of the studies includes treatment of the cells with an active agent, staining the cells with fluorescent dyes, and then monitoring the response of the active agents over time via flow cytometry. Several authors demonstrated monitoring of bacteria viability and vitality using flow cytometry, including various strains of Escherichia coli (Mason, D. J., et al., J Appl Bacteriol (1995) 78(3): 309-15; Jepras, R. I., et al., Appl Environ Microbiol (1995) 61(7):2696-2701; Kaprelyants, A. S. and D. B. Kell Journal of Applied Bacteriology (1992) 72:410-422), Salmonella typhimurium (Mason, D. J., et al., (1995), supra), Staphylococcus spp. (Mason, D. J., et al., (1995), supra; Jepras, R. I., et al., (1995), supra, Lloyd, D. and A. J. Hayes, FEMS Microbiol Lett (1995) 133:1-7; Langsrud, S. and G. Sundheim J Appl Bacteriol (1996) 81(4):411-8), Bacillus subtilis (Diaper, J. P., et al., Appl Microbiol Biotechnol (1992) 38(2):268-72), Pseudomonas spp. (Jepras, R. I., et al., Appl Environ Microbiol (1995) 61(7): 2696-2701; Langsrud, S. and G. Sundheim J Appl Bacteriol (1996) 81(4): 411-8) and Micrococcus luteus (Kaprelyants, A. S. and D. B. Kell, Journal of Applied Bacteriology (1992) 72:410-422).

Subsequently, a number of groups demonstrated rapid detection of antibiotic susceptibility or resistance via flow cytometric measurements of cultured bacteria (Martinez, O. V., et al., Cytometry (1982) 3(2):129-33; Suller, M. T., et al., J Antimicrob Chemother (1997) 40(1):77-83; Durodie, J., K. et al., Cytometry (1995) 21(4):374-7; Ordonez, J. V. and N. M. Wehman, Cytometry (1993) 14(7): 811-8; Pore, R. S. J Antimicrob Chemother (1994) 34(5):613-27; Roth, B. L., et al., Appl Environ Microbiol (1997) 63(6):2421-31; Mason, D. J., et al. J Microsc, (1994) 176(Pt 1):8-16; Mason, D. J. and V. A. Gant, J Antimicrob Chemother, (1995) 36(2): 441-3; Gant, V. A., et al., J Med Microbiol, (1993) 39(2): 147-54). and directly from clinical specimens (Cohen, C. Y. and E. Sahar, J Clin Microbiol (1989) 27(6):1250-6). The bacteria studied include both gram negative and gram positive organisms; Escherichia coli (Martinez, O. V., et al., Cytometry (1982) 3(2):129-33; Durodie, J., K. et al., Cytometr (1995) 21(4): 374-7; Roth, B. L., et al., Appl Environ Microbiol (1997) 63(6):2421-31; Mason, D. J., et al., J Microsc (1994) 176(Pt 1):8-16), Bacillus cereus (Roth, B. L., et al., Appl Environ Microbiol (1997) 63(6):2421-31), S. aureus (Suller, M. T., et al., J Antimicrob Chemother (1997) 40(1):77-83; Ordonez, J. V. and N. M. Wehman, Cytometry (1993) 14(7):811-8; Roth, B. L., et al., Appl Environ Microbiol (1997) 63(6):2421-31; 44; Cohen, C. Y. and E. Sahar, (1989), supra), Staphylococcus epidermidis (Cohen, C. Y. and E. Sahar, (1989), supra), Streptococcus pyogenes (Cohen, C. Y. and E. Sahar, (1989), supra), Klebsiella pneumoniae (Cohen, C. Y. and E. Sahar, (1989), supra), Pseudomonas aeruginosa (Cohen, C. Y. and E. Sahar, (1989), supra), P. stutzeri (Cohen, C. Y. and E. Sahar (1989), supra), Proteus mirabilis (Cohen, C. Y. and E. Sahar (1989), supra), and Enterobacter spp. (Cohen, C. Y. and E. Sahar, (1989), supra).

Several notable results come from this body of work. First, researchers were able to accurately determine sensitivity to various antibiotics, including ampicillin (Roth, B. L., et al., Appl Environ Microbiol (1997) 63(6):2421-31; Mason, D. J., et al., J Microsc (1994) 176(Pt 1):8-16), amoxicillin (Roth, B. L., et al., Appl Environ Microbiol (1997) 63(6):2421-31), penicillin G (Suller, M. T., et al., J Antimicrob Chemother (1997) 40(1):77-83, 41, Roth, B. L., et al., (1997), supra], vancomycin (Suller, M. T., et al., J Antimicrob Chemother (1997) 40(1):77-83; Roth, B. L., et al., (1997), supra), gentamicin (Mason, D. J., et al., J Microsc (1994) 176(Pt 1):8-16), ciprofloxacin (Durodie, J., K. et al., Cytometr (1995) 21(4): 374-7); Mason, D. J., et al., J Microsc (1994) 176(Pt 1):8-16), methicillin (Suller, M. T., et al., J Antimicrob Chemother (1997) 40(1):77-83), amoxicillin (Durodie, J., K. et al., Cytometr (1995) 21(4):374-7), mecillinam (Durodie, J., K. et al., Cytometr (1995) 21(4):374-7), chloramphenicol (Durodie, J., K. et al., Cytometr (1995) 21(4):374-7), trimethoprim (Durodie, J., K. et al., Cytometr (1995) 21(4):374-7), sodium cefazolin (Martinez, O. V., et al., Cytometry (1982) 3(2):129-33), moxalactam (Martinez, O. V., et al., Cytometry (1982) 3(2):129-33), cefamandole lithium (Martinez, O. V., et al., Cytometry (1982) 3(2):129-33), oxacillin (Ordonez, J. V. and N. M. Wehman, Cytometry (1993) 14(7):811-8), and amikacin (Cohen, C. Y. and E. Sahar, J Clin Microbiol (1989) 27(6):1250-6). The antibiotics spanned various antibiotic classes (β-lactams, cephalosporins, fluoroquinolones, glycopeptides, aminoglycosides, etc.), which have distinct mechanisms of action, ranging from inhibiting cell wall biosynthesis to interfering with protein synthesis or DNA replication. The susceptibility was well correlated with standard disk diffusion or dilution methods.

Second, antibiotic susceptibility was determined very rapidly (30 min-2.5 hrs, depending on the bacterial species under study and the protocol used). The rapid results were achieved because the technique does not require time for population growth, but instead interrogates the direct effect of antibiotics on cellular viability for a small number of bacteria.

Third, a consensus of the utility of various fluorescent dyes emerged. Although several dyes were used to demonstrate rapid antibiotic susceptibility via flow cytometry, including Rhodamine 123 (Mason, D. J., et al., J Appl Bacteriol (1995) 78(3):309-15; Kaprelyants, A. S. and D. B. Kell, (1992), supra, Langsrud, S. and G. Sundheim J Appl Bacteriol (1996) 81(4): 411-8), Sytox green (Langsrud, S. and G. Sundheim J Appl Bacteriol (1996) 81(4): 411-8; Roth, B. L., et al., (1997), supra), LIVE stain (Langsrud, S. and G. Sundheim J Appl Bacteriol (1996) 81(4): 411-8), carbocyanines (e.g. 3,3'-dipentyloxacarbocyanine iodide, Di005(3)) (Mason, D. J., et al., (1995), supra; Ordonez, J. V. and N. M. Wehman, *Cytometry* (1993) 14(7):811-8), propidium iodide (Jepras, R. I., et al., *Appl Environ Microbiol* (1995) 61(7): 2696-2701; Roth, B. L., et al., (1997), supra), ethidium monoazide (Jepras, R. I., et al., *Appl Environ Microbiol* (1995) 61(7): 2696-2701), FITC (Durodie, J., et al., *Cytometry*, (1995) 21(4):374-7), ethidium bromide (Martinez, O. V., et al., *Cytometry* (1982) 3(2):129-33; Jepras, R. I., et al., (1995), supra; Cohen, C. Y. and E. Sahar, (1989), supra), fluorescein esters (Jepras, R. I., et al., (1995), supra), calcafluor white (Mason, D. J., et al., (1995), supra), and an oxonol (bis-(1,3-dibutyl-barbituric acid)trimethine oxonol, $DiBAC_4(3)$) (Mason, D. J., et al., (1995), supra; Suller, M. T., et al., *J Antimicrob Chemother* (1997) 40(1):77-83; Mason, D. J., et al., *J Microsc* (1994)176 (Pt 1):8-16), only a couple appear to be well-suited for a broad-based diagnostic technique. In one embodiment, detection as described herein, is performed using flow cytometry methods. In an alternate embodiment, detection is not performed using flow cytometry methods.

Although it has been shown that antibiotic susceptibility/resistance can be assessed on intact bacterial cells using flow cytometry methods, this method still takes between 30 minutes and 2.5 hours to produce a result. The discovery that shear stress can expedite the process of detecting bacterial antibiotic susceptibility permits a result to be determined within 1-30 minutes. In one embodiment, the bacteria can be tested within the range of 5-30 minutes inclusive; in alternate embodiments the bacteria can be tested in 5-25 minutes, 5-20 minutes, 5-10 minutes, 5-8 minutes, 1-2 minutes, 1-5 minutes, 1-10 minutes, 1-15 minutes, 15-20 minutes, 15-25 minutes or 15-30 minutes. In some embodiments, a result is produced using the methods and devices described herein within 30-120 minutes. It is preferred that an appropriate antibiotic can be selected for treatment of an individual within the time frame of a typical doctor's visit. Such a visit generally lasts about 20 minutes, so to develop a method that would enable proper targeted antibiotic-bacterial matching in less than 20 minutes would significantly reduce costs associated with healthcare professionals' time. Thus, it is contemplated herein that a sample is obtained and analyzed within this time frame so that the doctor can appropriately prescribe an antibiotic that will be beneficial in treatment of the individual.

Optimization of the Methods Described Herein

Herein are described exemplary considerations for optimizing various parameters including fluorescent stains, growth conditions (medium, temperature etc.), flow rates and addition of chemical stressors.

As described herein, exemplary stains for use with the methods and devices described herein are Sytox green and $DiBAC_4(3)$. Both stains meet the criteria of effectively staining gram positive and gram negative bacteria, are non-toxic, only stain damaged cells, can be used directly in the growth medium, and do not require additional pretreatment processing steps. Additionally, both stains are commercially available from Molecular Probes. The bacteria are first bound to the glass slides and the stain is flowed past the cells to stain them. The staining conditions can be varied to identify the best staining parameters, including stain concentration, ranging from 0.025-0.5 µM for Sytox (Langsrud, S. and G. Sundheim, *J Appl Bacteriol* (1996) 81(4):411-8; Roth, B. L., et al., *Appl Environ Microbiol* (1997) 63(6):2421-31) and 0.25-2.0 mg/L for $DiBAC_4(3)$ (Suller, M. T., J. M. Stark, and D. Lloyd *J Antimicrob Chemother* (1997) 40(1):77-83; Mason, D. J., et al., *J Microsc* (1994) 176(Pt 1):8-16), and change in stain intensity over time to identify the time required for staining. The utility of the stains in the flow cell are assessed by comparing live cells grown to mid-log phase, and dead cells (both heat-killed and gramicidin-treated). These controls provide the range of signals expected and allow calibration of the image capture software.

The non-toxicity of the stains at the optimized concentrations can be confirmed via standard quantitative plating techniques performed on stained and unstained bacterial suspensions. For example, to test *S. aureus* in mid-log phase, cultures can be inoculated with MHB+2% NaCl to a density of $~10^7$ cfu/ml and the culture is incubated at 35° C. until the optical density of the culture at 650 nm reaches ~0.35. The bacteria are harvested by centrifugation, washed once, and then immobilized on the glass slide surface. The Sytox stain has a low level of background that allows cells to be visualized without the addition of other dyes (Roth, B. L., et al., *Appl Environ Microbiol* (1997) 63(6):2421-31). However, a positive control dye can be added to the cells to assure that an adherent population of cells has been achieved and that a lack of signal does not mean an absence of cells. In one embodiment it is preferred to add as few stains to the experiment as possible so as not to disrupt the interactions with the antibiotics and thus Sytox may be preferred for this reason.

Once the staining procedure is determined for a particular fluorescent dye, the flow parameters can be varied to ascertain the level of mechanical stress via shear stress necessary to produce cell damage of a particular strain of bacteria in order to detect antibiotic susceptibility.

An antibiotic (e.g., oxacillin) can be added at the minimum inhibitory concentration (MIC), and also 0.1×, 0.5×, 5×, and 10×MIC to optimize the assay for a particular set of flow parameters.

The flow parameters to be used can include application of static flow at various velocities and application of increasing flow velocities at various ramping speeds. It is further contemplated herein that a constant shear stress is applied over time or an increasing shear stress is applied over time. The flow parameters to be used can also include intermittent flows varying between no flow and fast flows, or slower flows and faster flows, or any combination thereof.

Additionally, the effect of various growth environments for the bacteria can be tested. It is likely that at least minimal media is required to sustain the bacteria and allow them to repair any damage caused by mechanical stress in combination with the antibiotics. Thus, in general the methods described herein use standard media as the fluid (i.e. Mueller Hinton broth), but can be varied in terms of concentration, media type, and temperature of the fluid. The optimization of the bacterial environmental conditions is especially important if the cells in the absence of antibiotics are rapidly damaged under mild shear conditions.

Bacterial Strains

Optimization of the methods described herein can be performed using two strains of bacterial cells grown to logarithmic phase (MSSA USA300 and MRSA USA300). Initial testing with logarithmic phase bacteria was chosen because they are more likely to be adherent due to higher expression of adhesins and their peptidoglycan layer is likely to be less cross-linked and thick compared to stationary-phase cells and the cells are more metabolically active allowing for faster response to damage.

It is further contemplated herein that optimal conditions can vary from strain to strain. Since different strains are often encountered in a clinical setting, this information is important for assessing the utility of the diagnostic methodology. Although it is contemplated herein that there will be strain variability, it is anticipated that the bacteria will behave similarly enough to permit the use of a single protocol for testing all the strains. This expectation is based on the fact that bacterial families (e.g., staphylococci) are genetically quite similar to each other and thus have similar cell structures, which will be the main component in their responsiveness to shear stress.

In terms of bacterial strain effects, two sources of variability are expected: differences in response time and adhesion strength. Thus one will need to quantify the differences and then adjust the protocol to accommodate them. For example, if strain A takes 5 min to demonstrate susceptibility, but strain B takes 30 min, then the protocol will require at least 30 min to determine susceptibility for an unknown strain. Because the adhesin and capsule expression will differ among strains, bacteria can be covalently linked to the substrate.

Another strain difference is that although most strains of *S. aureus* with reduced susceptibility to methicillin produce the low-affinity penicillin binding protein PBP2a, encoded by the mecA gene, some strains produce borderline methicillin-resistance due to hyperproduction of beta lactamase. For these studies, a beta-lactamase inhibitor, such as clavulanic acid can be included, although clinicians often prefer to prescribe vancomycin in these cases as opposed to Augmentin (amoxicillin with clavulanic acid). As described previously, different combinations of antibiotics can be tested in different channels simultaneously.

Bacterial Growth Phase

The method can be widely applied after assessing and characterizing any variability due to the growth phase of the bacteria. First, the technique can be inserted into the current clinical microbiology laboratory workflow by simply replacing the antibiotic susceptibility testing that follows primary culture. In this embodiment, the primary culture grown to stationary phase seeds the susceptibility testing apparatus. Alternatively, the technique is coupled with a rapid isolation technique to detect antibiotic susceptibility of bacteria obtained directly from a clinical sample. This latter method has greater clinical impact on patient management by providing antibiotic susceptibility information in time for the initial treatment decision.

In addition, bacteria can be in various growth phases providing both intra-sample and inter-sample variations. The growth phase of the bacteria influences the results in several ways. First, bacteria in lag or stationary phase causes bacteria to respond more slowly to environmental stressors, thus there can be differences in time to results as compared to actively growing bacteria. Second, the adherence to the capture agents varies due to differing expression of adhesins and capsule production in post-exponential phase cultures. This can necessitate covalent bonding to the substrate. Third, the peptidoglycan layer is more cross-linked and thick in stationary phase than in logarithmic phase. Optimization of the method can be performed by testing MSSA and MRSA strains at lag-phase, logarithmic phase, and stationary phase. To test *S. aureus* in lag phase, a culture is inoculated (MHB+2% NaCl to a density of $\sim 10^7$ cfu/ml) and incubated at 35° C. for 90 min. The bacteria are harvested by centrifugation, washed once, and then immobilized on the glass slide surface. The cells should be tested immediately. To test *S. aureus* in stationary phase, cells are cultured as above, but overnight.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Herein is described a method for applying shear stress and/or chemical stress to bacterial cells to enable rapid detection of antibiotic susceptibility. The purpose of the shear stress is to strain the cells, specifically by damaging the cell wall. Methicillin, as with other antibiotics in its class, inhibits the biosynthesis of the cell wall. Thus it was hypothesized that damage to the cell wall in the presence of antibiotics causes cell damage and eventual death in susceptible strains, whereas resistant strains will be able to repair themselves. The imposed mechanical strain will shorten the time to detection significantly, and detection may be achieved on the order of minutes to tens of minutes. In addition, adding mechanical stress to the bacteria will also activate other biochemical pathways that are targeted by antibiotics with other mechanisms of action (e.g., other than biosynthesis of the cell wall), therefore this methodology is not limited to antibiotics that act by inhibiting cell wall biosynthesis.

Example 1

Exemplary Device for Determining Antibiotic Susceptibility

Described herein is an exemplary device for determining antibiotic susceptibility/resistance of bacteria. The device comprises a flow cell that enables controlled shear stress to be applied to immobilized bacterial cells in the presence of growth media. Fluid will flow through the channel, simultaneously applying shear stress to the bacterial cells and delivering growth media, fluorescent stain, and antibiotic. In some embodiments, the fluorescent stains are chosen such that they do not enter the cells unless the cell wall is permeabilized or the membrane potential changes, and thus will not interfere with cellular repair. If the bacteria are susceptible to the antibiotic, the stress on the cells will eventually cause the cells to die and thus become fluorescently stained. If the bacteria are resistant to the antibiotic, they will be able to repair their cell walls in the presence of the antibiotics and therefore remain unstained.

In one embodiment, the device comprises a flow cell comprised of two glass slides (one functionalized and one non-functionalized) separated by a gasket of silicone rubber that defines a single channel ($\sim 500$ μm wide). The flow cell design allows standard glass slide functionalization methods to be used to immobilize the bacteria to the base of the flow channel. After bacterial immobilization, the glass slides and silicone rubber are clamped together using a metal housing designed to be integrated into the microscope stage. The housing is attached to a syringe pump to control the shear stress on the immobilized bacteria. The bacteria can be monitored by a microscope with phase/contrast and fluorescence capabilities. The attached camera can acquire images as fast as 10/sec, using e.g., ImageJ (available on the world wide web at rsbweb.nih.gov/ij/) to analyze the data.

The shear rates in the system were estimated using an 'infinite' parallel plates (i.e. negligible edge effects) fluid dynamics model which states that the shear rate (du/dx) is $$\frac{\partial u}{\partial x} = \frac{6Q}{wh^2}$$

where Q is the bulk flow rate through the channel, w is the width of the channel, and h is the height of the channel. With a ~300 μm wide by 500 μm high channel attached to a KDS100 syringe pump (flow rates from 0.1 μL/hr to 426 mL/hr), shear rates up to 9,000 s$^{-1}$ can be achieved.

For the initial prototype system, an Olympus IX81 microscope equipped with fluorescence and phase/contrast capabilities was used to gather initial data and to define any additional system requirements. The following three additions were added: a motorized microscope stage, integrated temperature control, and a recirculating pump. The stage of the microscope is motorized to allow a series of alternating photos of a channel with antibiotics and one without antibiotics. A temperature control can be incorporated into the device to maintain the bacterial cells in log phase. Initial experiments have demonstrated that a recirculating fluidic design can be used to maintain shear forces over a longer period of time than is allowed with the syringe pump, which needs to be re-filled every 5-10 mins. Fluidics connections can include independent loops for re-circulating warmed growth media (up to 40° C.) via a water bath, but maintaining flexibility in the design to allow a single pass fluidic path if recirculation is not optimal. The fluidic pathway can include syringe junctions for introduction of defined quantities of chemicals (e.g. antibiotics).

The flow cell design can be extended to include multiple channels of identical dimensions. In the prototype system, the channels were hand cut from a silicone rubber sheet (thickness 230 μm). Although this method is convenient for gathering initial data, the manufacturing method can be altered to provide defined and reproducible channel dimensions. At least two alternate methods of cutting can be used, which include laser ablation and water jet cutting. UV-nanosecond and IR-femtosecond lasers have also been shown to be effective tools to ablate silicone rubber at the channel sizes described herein without chemically modifying the material. The alternative solution is water jet cutting which would produce appropriate channels, but the minimum feature size is 500-1000 μm.

Example 2

Method for Determining Antibiotic Susceptibility Functionalization of Slides

Capture agent proteins for immobilizing bacteria can be purchased from commercial sources in purified form (Sigma Aldrich) and nonspecifically bound to a glass slide following a basic protocol similar to coating microtiter plates that has been used in other flow cell studies of *S. aureus* (Shenkman, B., et al., *Infect Immun* (2001) 69(7):4473-8; Mascari, L., et al., *Biotechnol Bioeng* (2003) 83(1):65-74; Mascari, L. and J. M. Ross, *Ann Biomed Eng* (2001) 29(11):956-62; Mohamed, N., et al., *Infect Immun* (1999) 67(2): 589-94; Brouillette, E., et al., *Vaccine* (2002) 20(17-18):2348-57). Optimal coating conditions can be determined empirically.

Briefly, the capture agent is resuspended in a buffer (either 0.05 phosphate buffer pH 7 or 0.05M carbonate/bicarbonate buffer pH 9.6), and a small volume is placed on the glass slide. The slide is incubated at 37° C. in a humid chamber for 1-2 hrs. The slide is rinsed and then blocked overnight with a blocking agent, such as 1% non-fat milk protein or BSA. In some embodiments, a glass slide is the preferred bacterial capture substrate because of the superior optical properties, availability of chemically activated surfaces, substrate flatness, geometric compatibility with standard microscopes, and low cost. However, it is also possible to use fibrinogen or fibronectin immobilized on polystyrene surfaces.

Several combinations and concentrations of the three capture agents (ranging from 1 to 100 μg/ml) are tested to determine the optimal ratio and concentration for tight binding of *S. aureus*. As the USA300 strain does not produce capsule (Montgomery, C. P., et al., *J Infect Dis* (2008)), it is well suited for initial adherence studies. It carries genes encoding staphylococcal adhesins that bind to fibronectin, fibrinogen, and elastin.

*Staphylococcus aureus*: an Exemplary Antibiotic Resistant Bacterium

*Staphylococcus aureus* is an exemplary bacterium that exhibits antibiotic resistance and is used herein to optimize the methods and devices described herein. *S. aureus* was chosen as a model system to test the rapid detection of methicillin-resistance because *S. aureus* is very clinically relevant, is widespread and methicillin is specific for targeting cell wall biosynthesis.

1. Antibiotic Resistance of *Staphylococcus aureus*

The number of *S. aureus* infections is increasing, as is the resistance of *S. aureus* to a variety of antibiotics. Methicillin-resistant *Staph. aureus* (MRSA) account for 40%-60% of nosocomial *S. aureus* infections in the U.S., and many of these strains are multi-drug resistant. Notorious for decades as a major source of nosocomial infections, *S. aureus* has recently taken on a new role in causing an escalating number of community-acquired infections in hosts without significant predisposing risk factors. Virulent community-acquired MRSA strains are becoming more prevalent across the U.S. and Europe.

Methicillin resistance in staphylococci is caused by the expression of PBP2a encoded by the mecA gene that is located on a genetic element called the staphylococcal cassette chromosome (SCC). SCCmec is a group of mobile DNA elements of 21 to 67 kb that are found integrated into the chromosome of MRSA strains. Unlike hospital-acquired MRSA strains that carry large SCCmec elements and show a somewhat slower growth rate than methicillin-sensitive strains, the community-acquired MRSA strains often carry SCCmec type IV or V elements and show no defect in growth rate. The latter elements are smaller in size than the SCCmec types I, II, and III found in hospital-acquired MRSA, and their dissemination has been observed globally (Baggett, H. C., et al. *J Infect Dis*, (2004) 189(9):1565-73; David, M. D., et al. *J Hosp Infect* (2006) 64(3):244-50; Gilbert, M., J. *CMAJ* (2006) 175(2):149-54; Gosbell, I. B., et al. *Pathology* (2006) 38(3):239-44; Kazakova, S. V., J. C. et al. *N Engl J Med* (2005) 352(5):468-75). Many of the community-acquired MRSA strains produce the Panton-Valentine leukocidin (PVL), and this trait correlates with increased strain virulence (Baggett, H. C., et al., (2004), supra). PVL-producing *S. aureus* isolates have been associated with skin abscesses, as well as with necrotizing pneumonia, and often infect young and previously healthy patients (Baggett, H. C., et al., (2004), supra; Gillet, Y., et al. *Lancet* (2002) 359(9308):753-9; Muller-Premru, M., et al., *Eur J Clin Microbiol Infect Dis* (2005) 24(12):848-50).

Not only has resistance to methicillin among *S. aureus* isolates become markedly more common, but also numerous *S. aureus* strains with reduced susceptibility to vancomycin have been reported. Seven clinical isolates of *S. aureus* that carry the vanA resistance gene and are fully resistant to vancomycin have been reported. These isolates are also methicillin resistant (*MMWR Morb Mortal Wkly Rep*, (2002) 51(26); *MMWR Morb Mortal Wkly Rep* (2004) 53(15): 322-3; Chang, S., et al. *N Engl J Med* (2003). Because *S. aureus* cannot always be controlled by antibiotics and because MRSA isolates are becoming increasingly prevalent in the community, additional control strategies are sorely needed.

The mechanism of action of β-lactam antibiotics, such as penicillin and methicillin, is to inhibit bacterial cell wall (peptidoglycan) biosynthesis. Penicillin binding proteins (PBPs) are membrane bound DD-peptidases that have evolved from serine proteases, and their biochemical activity is mechanistically similar (Ghuysen, J. M., *Trends Microbiol*, (1994) 2(10):372-80; Waxman, D. J. and J. L. Strominger, *Annu Rev Biochem*, (1983). 52: p. 825-69). These enzymes catalyze the transpeptidation reaction that cross-links the peptidoglycan of the bacterial cell wall. The β-lactam antibiotics are stereochemically related to D-alanyl-D-alanine (Ghuysen, J. M., *Trends Microbiol*, (1994) 2(10):372-80) and are substrate analogs that covalently bind to the PBP active-site serine, inactivating the enzyme. PBPs 1, 2, and 3, which have high affinity for most β-lactam antibiotics, are essential for cell growth and for the survival of susceptible strains, and binding of β-lactams by these PBPs is lethal (Chambers, H. F. and M. Sachdeva, *J Infect Dis* (1990) 161(6):1170-6; Georgopapadakou, N. H., et al., *Antimicrob Agents Chemother* (1986) 29(2):333-6). Methicillin-resistance in staphylococci has been termed intrinsic because it is not due to the destruction of the antibiotic by β-lactamase, but is instead provided by penicillin-binding protein 2a (PBP2a) (reviewed in (Chambers, H. F., *Clin Microbiol Rev* (1997) 10(4):781-91). In methicillin-resistant cells, PBP2a, with its low affinity for binding β-lactam antibiotics (Brown, D. F. and P. E. Reynolds *FEBS Lett* (1980) 122(2):275-8; Hartman, B. J. and A. Tomasz, *J Bacteriol* (1984) 158(2):513-6; Utsui, Y. and T. Yokota *Antimicrob Agents Chemother* (1985) 28(3):397-403; Hayes, M. V., et al., *Antimicrob Agents Chemother* (1981) 29:119-122), can substitute for the essential functions of high-affinity PBPs (PBPs 1, 2 and 3) at concentrations of antibiotic that are otherwise lethal.

2. Immobilization of *S. aureus*

Staphylococcal adhesion to host tissue is mediated by surface exposed molecules named adhesins, which specifically bind to host receptors, including fibronectin, fibrinogen, thrombospondin, collagen, elastin, laminin, von Willebrand factor, osteopontin, bone sialoprotein, and vitronectin (Shenkman, B., et al. *Infect Immun* (2001) 69(7):4473-8; George, N. P., et al., *J Infect Dis* (2007) 196(4):639-46; George, N. P., et al., *Arterioscler Thromb Vasc Biol* (2006) 26(10):2394-400; Mascari, L. and J. M. Ross *Ann Biomed Eng* (2001) 29(11):956-62; Fallgren, C., et al., *Biomaterials* (2002) 23(23):4581-9; Herrmann, M., et al., *J Infect Dis* (1997) Herrmann, M., et al., *Infect Immun* (1991) 59(1):279-88; Herrmann, M., et al., *J Infect Dis* (1988) 158(4):693-701; Liang, O. D., et al., *J Biochem* (1994) 116(2):457-63; Smeltzer, M. S., et al. *Gene* (1997) 196(1-2):249-59; Brouillette, E., et al., *Vaccine* (2002) 20(17-18):2348-57; Vercellotti, G. M., et al., *Am J Pathol* (1985) 120(1):13-21). A study of the prevalence and chromosomal map location of *S. aureus* adhesin genes revealed that the genes for fibronectin- (fnbA and fnbB), fibrinogen- (fib and clfA), and elastin-binding proteins (ebpS) are highly conserved. From a review of the dynamic adhesion studies with *S. aureus*, preferred capture agents are fibrinogen and fibronectin. These proteins are especially well-suited for immobilization of *S. aureus* to glass slides since fibronectin binding proteins A and B, as well as clumping factor B (a fibrinogen binding protein), are expressed during the logarithmic phase of growth, whereas clumping factor A, the major *S. aureus* fibrinogen binding protein, is surface-associated in both logarithmic- and stationary-phase cultures. This is important since *S. aureus* may produce a capsule in the stationary growth phase, and in most strains the clumping factor protein will not be masked by the polysaccharide capsule. An additional gene (map) which encodes a broad specificity adhesin (MHC analog protein) that mediates low level binding of several proteins (osteopontin, collagen, bone sialoprotein, vitronectin, fibronectin, and fibrinogen) is also highly conserved and can be used as a capture agent, however it should be noted that this adhesin mediates only low-level binding and requires further optimization (see Optimization of Methods section herein).

The *Staphylococcus aureus* (MRSA strain MW2 and MSSA strain Sanger 476) were grown to log phase in Mueller-Hinton broth with 2% sodium chloride (MH2) and then immobilized on epoxide slides, which is a non-specific method for immobilizing bacteria and can be used instead of the adhesin mechanism. To immobilize the bacteria, 100 µL of culture was placed on the epoxide slide (Super-epoxy II, Telechem International) and incubated at 37° C. for 45 min in a humid environment. The immobilized cells were briefly rinsed with water and Block-it buffer (Telechem International) to quench any remaining un-reacted epoxide bonds. A series of control experiments was conducted including (1) varying protocols for immobilization to optimize cell density and viability, (2) varying shear rates to confirm it does not lead to significant loss of bacteria off of slide or due to cell death, and (3) varying concentrations of oxacillin and lysostaphin. In these preliminary studies, a set of conditions was found that permits differentiation between MRSA and MSSA strains in less than 15 min.

On two separate slides, MSSA (Sanger 476) and MRSA (MW2) strains were immobilized. The cells were assembled in channels of ~300 µm width and stained with 0.5 µM Sytox green in MH2. The immobilized cells were stressed with 0.6 ng/mL lysostaphin, ~4200 $s^{-1}$ shear rate, and 10 µg/mL oxacillin for 15 mins after a 40 min pretreatment with lysostaphin and shear alone. The lysostaphin concentration was chosen to be lower than the MIC (~1 ng/mL). The oxacillin concentration is greater than the MIC for the MSSA (0.5 µg/mL) and less than that for the MRSA (>16 µg/mL). More MSSA cells died during the course of the experiment than MRSA cells.

Strains of *Staphylococcus* useful for optimizing the methods described herein include several MRSA strains whose genomes have been sequenced:

(a) USA300 strain NRS384; highly virulent and has spread across the U.S. and other countries causing community-acquired staphylococcal infections (primarily skin and soft tissue infections). USA300 carries a type IV SCCmec element but does not make a capsule.

(b) Strain MRSA252; belongs to the clinically important EMRSA-16 clone that is responsible for half of all MRSA infections in the U.K. and is one of the major MRSA clones found in the U.S. (USA200). MRSA252 carries a type II SCCmec element and, produces a serotype 8 capsule.

(c) Strain MW2; belongs to the USA400 group. It carries a type IV SCCmec element, produces the Panton-Valentine leukocidin, and is associated with skin and soft tissue infections, as well as necrotizing pneumonia in children. USA400 was the most widespread community-acquired *S. aureus* strain prior to 2001 when USA300 emerged in the U.S. population. This strain also produces a type 8 capsule;

(d) A USA100 strain; represents the predominant U.S. hospital-acquired MRSA strain (also known as the New York/Japan clone). A useful strain of USA100 is strain NRS382 (McDougal, L. K., et al., *J Clin Microbiol* (2003) 41(11): 5113-20). NRS392 belongs to sequence type (ST) 5, and thus it is closely related to *S. aureus* strains N315 and Mu50 (both of these strains have been sequenced).

In addition, the following methicillin-sensitive *Staphylococcus aureus* (MSSA) strains can be used as a control for antibiotic susceptibility:

(a) MSSA476; a representative of an invasive community-acquired MSSA clone that was isolated from a 9-year old child with no predisposing risk factors who developed osteomyelitis and bacteremia; strain MSSA476 is a member of the USA400 pulsotype and is capsule negative;

(b) Strain Newman is a well-characterized MSSA strain whose genome was recently sequenced. Strain Newman is genetically very similar to the MSSA strain NCTC8325 and the MRSA strain COL, and it produces a serotype 5 capsule. Newman is a better choice than strain NCTC8325 because the latter carries a mutation in the rsbU locus that renders the strain deficient in sigma B regulated genes; and (c) MSSA USA300 strain.

Lysostaphin Susceptibility of MW2 and Sanger 476

Described herein is experimental evidence that the methods and devices described herein differentiate between a methicillin-resistant strain (MW2) and a methicillin-susceptible strain (Sanger 476) of *Staphylococcus aureus* in the presence of shear stress and chemical stress (lysostaphin with or without oxacillin). The difference was detectable within 15 mins of introducing oxacillin. In this experiment, lysostaphin was used to increase the stress on the *Staphylococcus* cells above that imposed by the fluidic shear. In the interpretation of these results it is important to understand the sensitivity of the two strains to lysostaphin. As published values were not readily available, the lysostaphin susceptibility of MW2 and Sanger 476 was empirically determined.

A classical microdilution broth method was used to determine the lysostaphin minimum inhibitory concentrations for strains MW2 and Sanger 476 (Jones, R. N., et al. Manual of clinical microbiology, A. Balows, J. W. J. Hausler, and H. J. Shadomy, Editors. 1985, American Society for Microbiology: Washington D.C. p. 972-977). Briefly, logarithmic-phase bacteria were cultivated in Mueller-Hinton cation-adjusted broth (MHB) and adjusted to a concentration of $1 \times 10^6$ CFU/mL. Sterile microtiter plates containing 100 µl of lysostaphin diluted in MHB were inoculated with 100 µl of the bacterial suspension to yield $5 \times 10^5$ CFU/mL. After overnight incubation at 37° C. overnight, the MIC for both strains was 0.06 µg/mL.

As the sensitivity to lysostaphin is the same for both strains, the results presented herein strongly demonstrate that shear stress can be used to rapidly determine antibiotic susceptibility.

Detecting Mechanical Strain on Bacterial Cells with $DiBAC_4(3)$

Studies with Sytox Green were successful in that the stain is very bright for dead cells with a low background of staining for the live cells. Since Sytox green works by staining the nucleic acids, it is effective mainly at the late stage of antibiotic action (when the cells are truly dead). Thus, to measure the antibiotic susceptibility in the system described herein with Sytox Green within tens of minutes, one needs to apply very high shear rates and additional chemical stress (lysostaphin).

On the other hand, $DiBAC_4(3)$ is a stain that measures changes in membrane potential and is therefore a more sensitive and earlier indicator of cellular damage. It was recently confirmed that $DiBAC_4(3)$ does stain cells under high stress when Sytox green does not stain them. As such, one can achieve rapid detection of antibiotic susceptibility with mechanical stress alone (i.e. no lysostaphin) when using $DiBAC_4(3)$ as the stain.

Example 3

Exemplary 4-Channel Flow-Cell

Figure 8A:
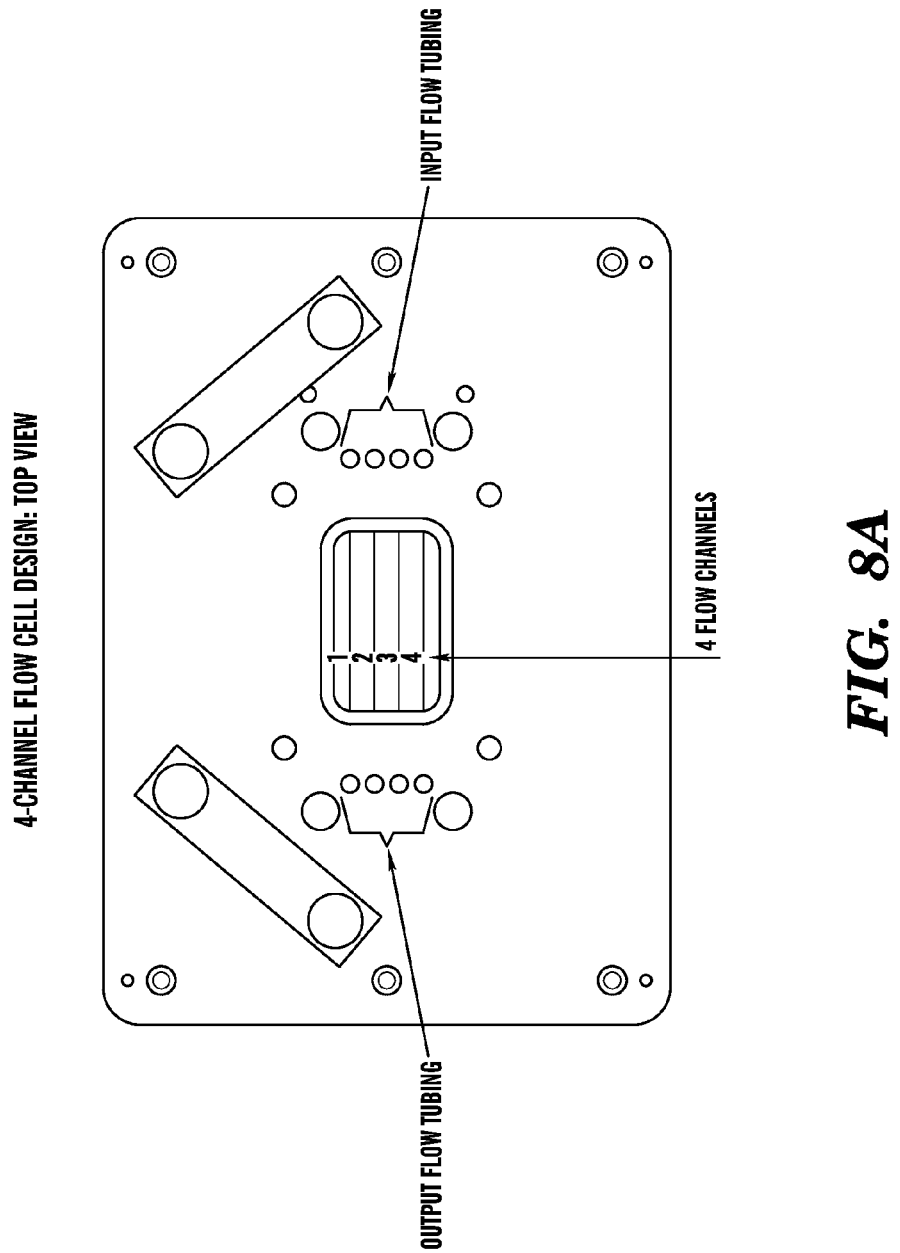
FIGS. 8A-B shows an exemplary 4-channel flow cell design for use with the methods described herein (8A), and exemplary software for automation of data collection using such a flow cell (8B).
Figure 8B:
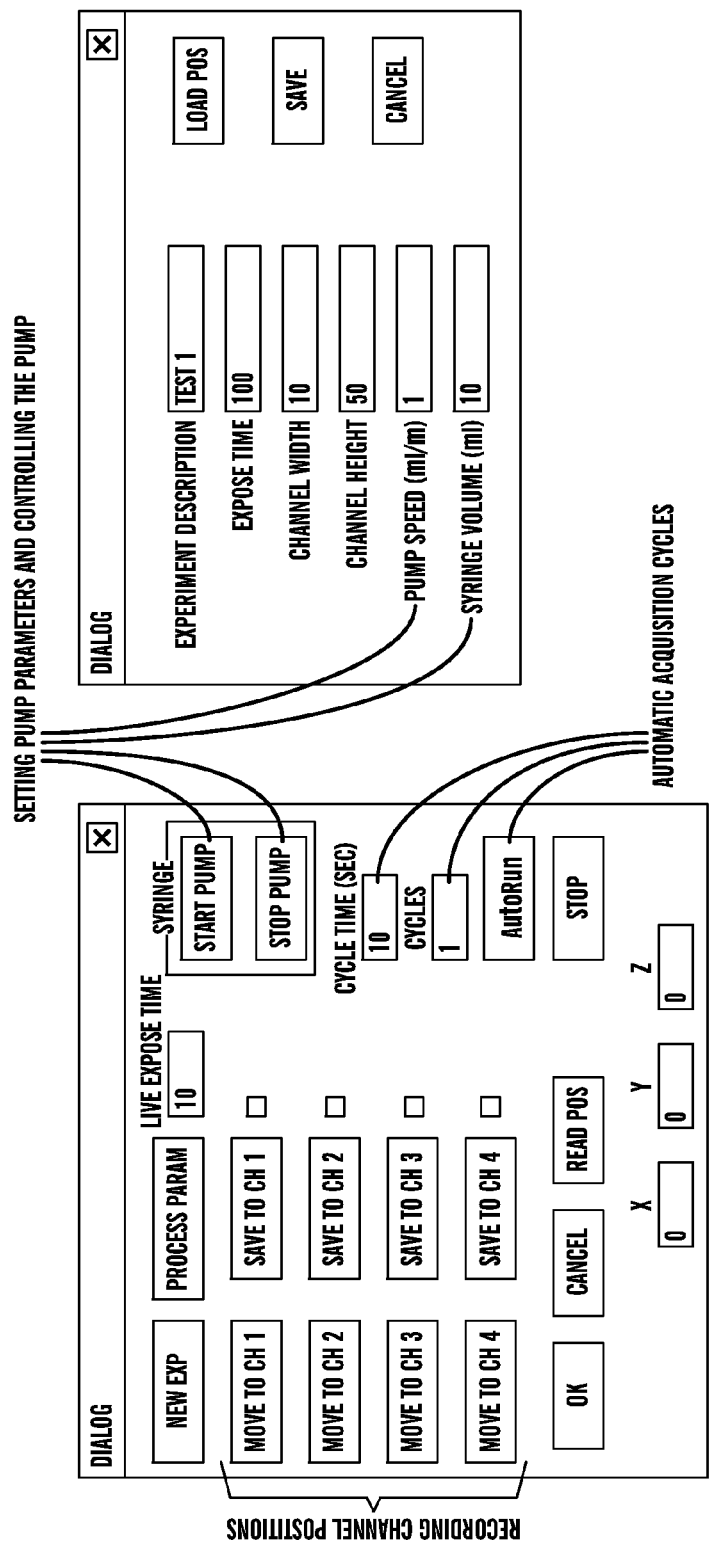

Also provided herein is an exemplary flow cell comprising four channels arranged in a parallel manner as shown herein in FIG. 8A. The flow cell can be used in conjunction with the instrument and software depicted in FIG. 8B.

This 4-channel arrangement was used to test a single strain of bacteria in the presence or absence of chemical stress (e.g., lysostaphin). The flow rate used in the channels was 1 mL/min and 0.5 µM Sytox Green was used to stain damaged or dying cells.

Figure 9A:
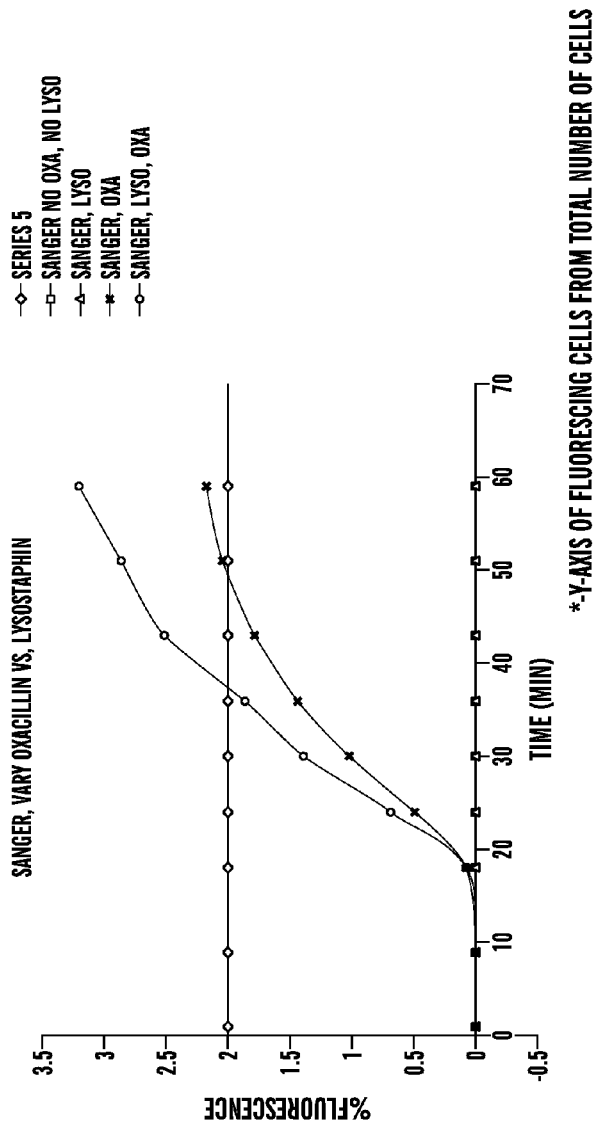
FIG. 9A-B shows representative data from a 4-channel flow cell testing the effect of chemical stress in the presence and absence of oxacillin in Sanger 476 methicillin sensitive cells (9A) or MW2 methicillin resistant cells (9B).
Figure 9B:
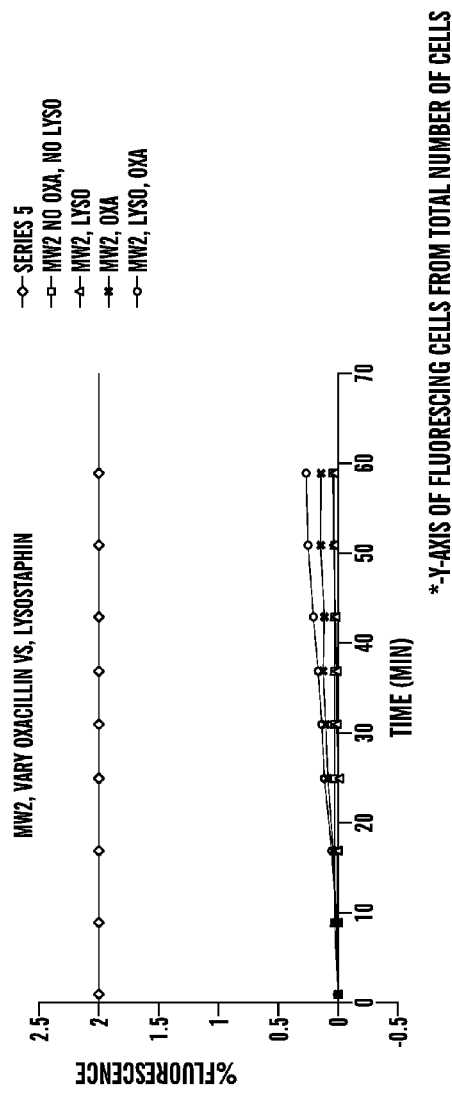

FIG. 9A shows data using a Sanger strain of *staphylococcus* that is susceptible to oxacillin treatment, while FIG. 9B shows data using a methicillin and oxacillin resistant strain of bacteria (MW2). In each experiment, bacteria in two channels were exposed to 0.7 ng/mL lysostaphin (lyso) in the presence or absence of the antibiotic oxacillin (oxa; 50 µg/mL). The four experimental groups are as follows: (i) control (no oxa; no lyso), (ii) lyso only; (iii) oxa only, and (iv) lyso and oxa together.

The level of fluorescence in Sanger cells in the channel treated with lyso alone was not substantially different from the level of fluorescence in the control channel. Fluorescence was increased at a time point of approximately 20 min in both the lyso/oxa treated Sanger group as well as the Sanger cells treated with oxa alone. However, the Sanger cells in the channel treated with both lyso and oxa died faster than the Sanger cells receiving oxa alone. These data indicate that chemical stress can be used to augment mechanical shear stress and increase the susceptibility of bacteria to antibiotic induced damage in an assay setting. Furthermore, these data demonstrate successful use of the methods and devices described herein.

FIG. 9B shows that there was no substantial increase in fluorescence of MW2 cells treated with oxacillin compared to control MW2 cells. This result is expected since the MW2 strain is resistant to oxacillin-mediated cell death. MW2 cells treated with lyso alone showed a small increase in fluorescence further confirming that chemical stress can be used successfully in a variety of bacterial strains with the methods and devices described herein.

Figure 10A:
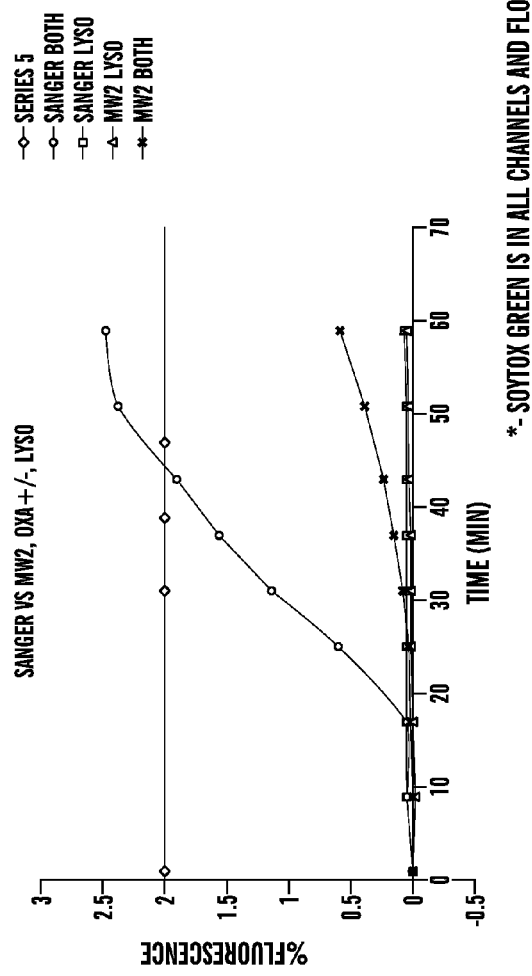
FIGS. 10A-B shows representative data from a 4-channel flow cell design testing two bacterial strains simultaneously in the presence or absence of lysostaphin, oxacillin or a combination thereof.
Figure 10B:
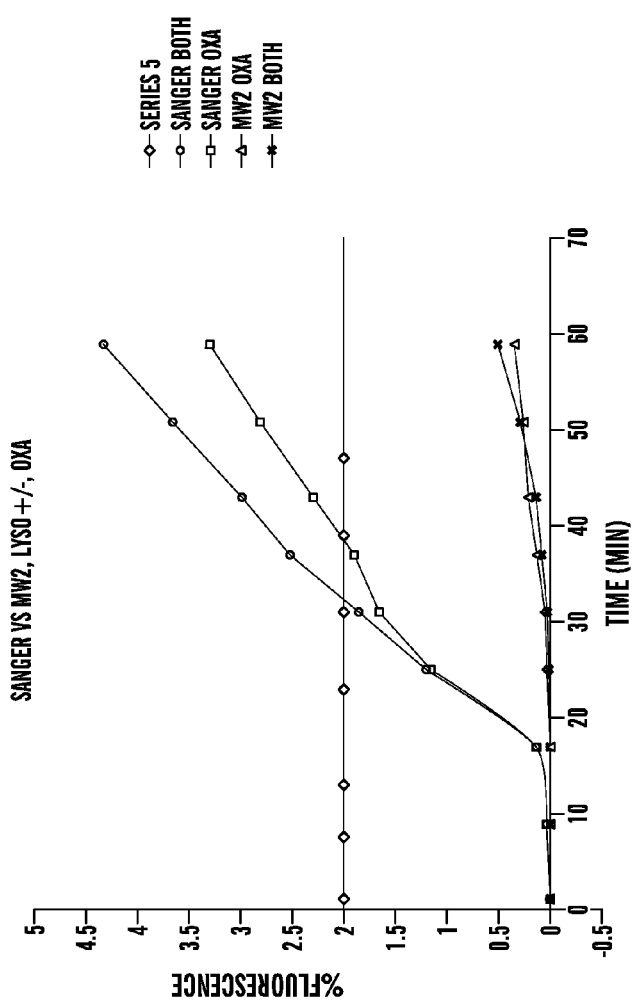
Figure 11:
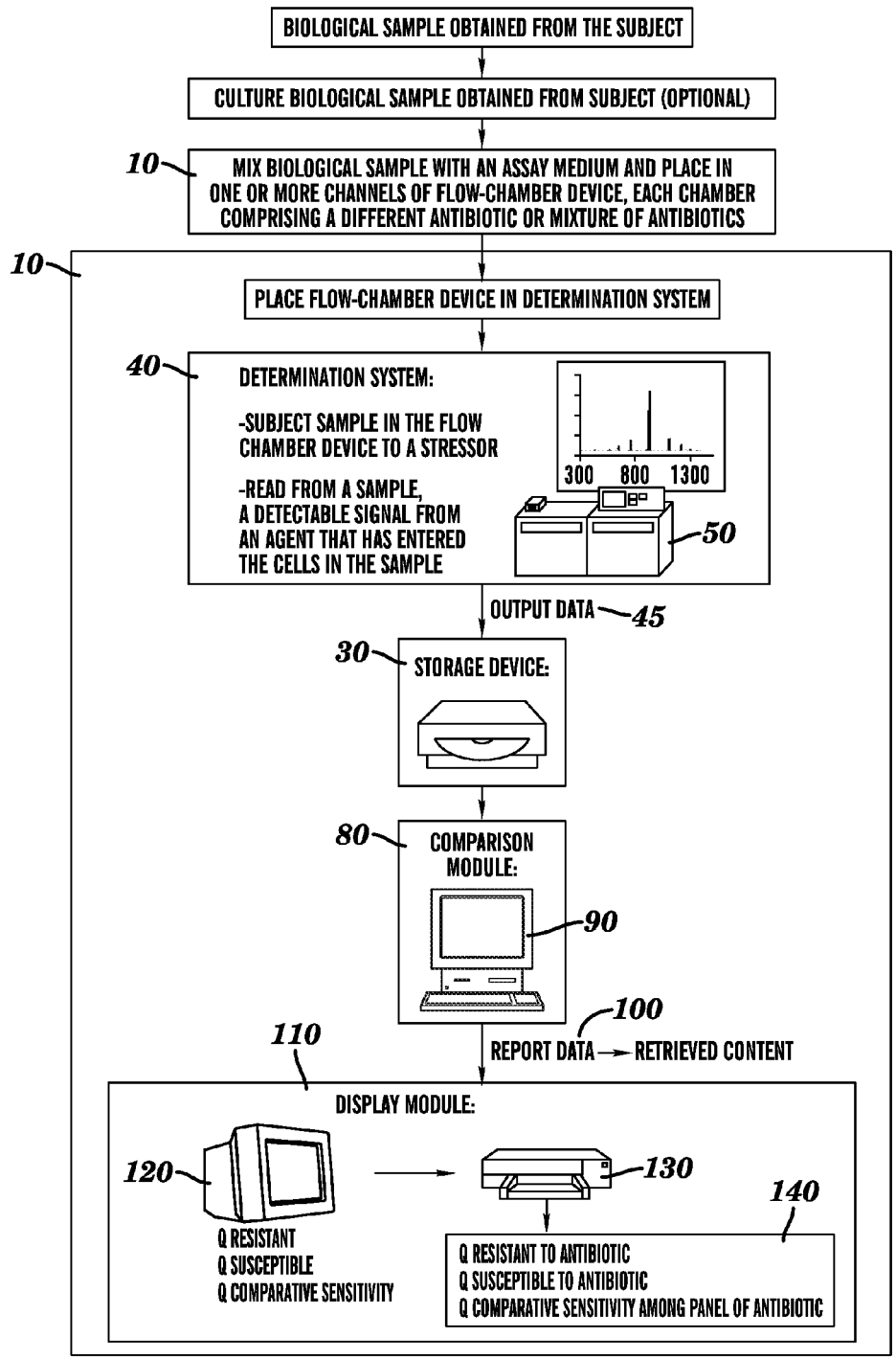
FIG. 11 shows an exemplary range of shear stress levels based on varying the width and height of the channels within the flow cell of the assay system.
Figure 12:
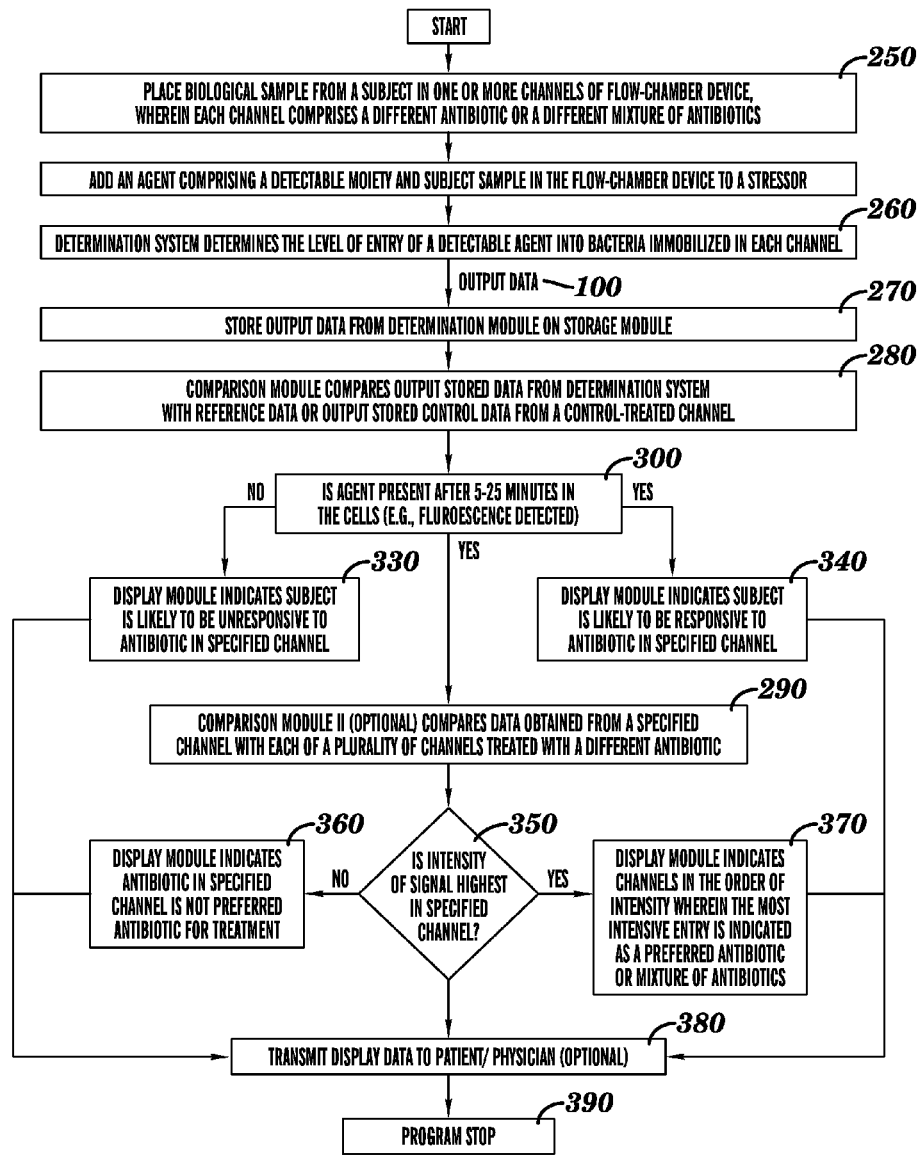
FIG. 12 is a block diagram showing an exemplary system for use with the methods described herein.
Figure 13:
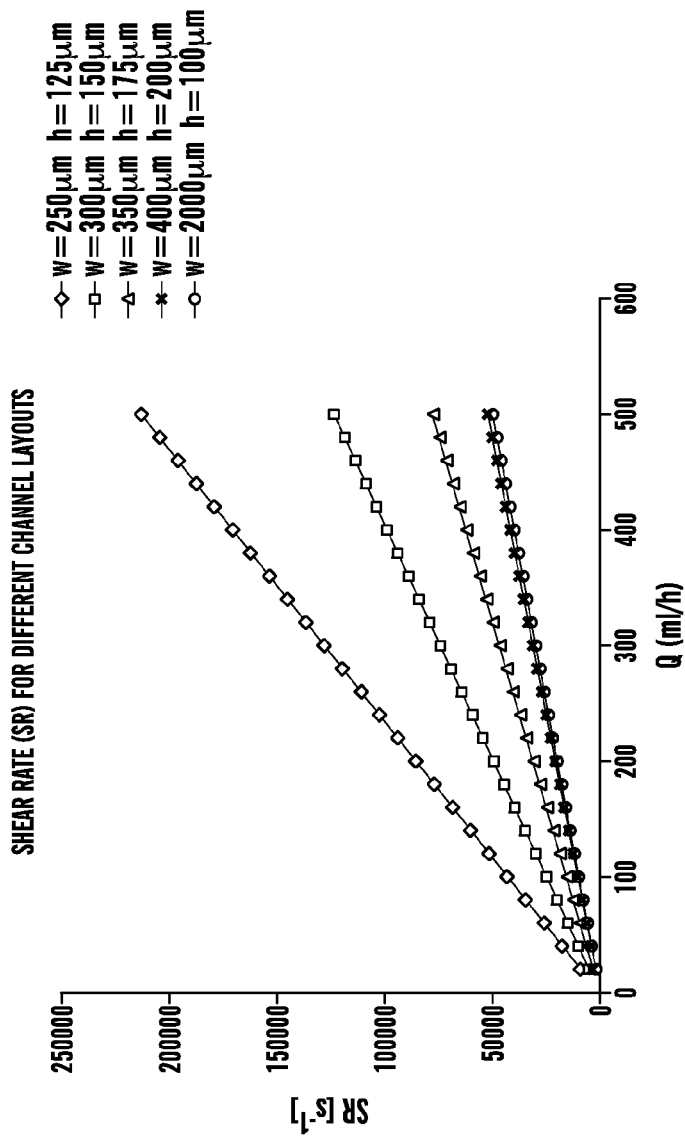
FIG. 13 is a block diagram showing exemplary instructions encoded on a computer readable medium for use with the devices and systems described herein.

The 4-channel system can also be used to test two bacterial strains simultaneously as shown herein in FIGS. 10A and 10B.

The invention claimed is:

1. A method for determining sensitivity of bacteria to an antibiotic, the method comprising:

(a) immobilizing the bacteria from a bacterial suspension by covalent attachment to a solid support, (b) contacting said immobilized bacteria with an agent comprising a reporter moiety, which preferentially binds to damaged bacterial cells,
(c) subjecting said immobilized bacteria to a stressor in the presence of an antibiotic without the need for bacterial growth phase,
(d) detecting a signal from said reporter moiety in said immobilized bacteria wherein said detecting is performed between 1 and 30 minutes from contacting said covalently immobilized bacteria with the stressor in the presence of the antibiotic, and
(e) comparing the signal from said immobilized bacteria in the presence of the antibiotic to a control comprising immobilized bacteria subjected to the stressor in the absence of the antibiotic,
wherein detection of an increase in said signal in the presence of an antibiotic compared to a control indicates that said bacteria are susceptible to said antibiotic, and wherein a signal that is comparable to the control in the presence of an antibiotic indicates that said bacteria are resistant to said antibiotic.

2. The method of claim 1, wherein said detecting is performed between 5 and 25 minutes from contacting said covalently immobilized bacteria with the agent and the stressor in the presence or absence of the antibiotic.

3. The method of claim 1, wherein said detecting step comprises detecting fluorescence.

4. The method of claim 1, wherein said reporter moiety comprises a fluorescent dye.

5. The method of claim 4, wherein said fluorescent dye detects gram negative and/or gram positive bacteria.

6. The method of claim 4, wherein said fluorescent dye is SYTOX green.

7. The method of claim 4, wherein said fluorescent dye is $DiBAC_4(3)$.

8. The method of claim 1, wherein said stressor comprises physical stress.

9. The method of claim 1, wherein said stressor comprises chemical stress.

10. The method of claim 1, wherein said stressor comprises physical and chemical stress.

11. The method of claim 1, wherein said stressor comprises lysostaphin, an endolysin, lysozyme, oxidative stress or a porin.

12. The method of claim 1, wherein said stressor comprises shear stress, osmotic stress, acidic pH or basic pH.

13. The method of claim 1, wherein said method comprises a high-throughput method.

14. The method of claim 1, wherein said bacteria are pathogenic bacteria.

15. The method of claim 14, wherein said pathogenic bacteria is one that infects or causes disease in a human host.

16. The method of claim 1, wherein the solid support is glass.

* * * * *